US009149231B2

(12) United States Patent
Fujita et al.

(10) Patent No.: US 9,149,231 B2
(45) Date of Patent: Oct. 6, 2015

(54) ALCOHOL-DRINKING DETECTING SYSTEM AND COMPUTER PROGRAM

(75) Inventors: Etsunori Fujita, Hiroshima (JP); Yumi Ogura, Hiroshima (JP); Shinichiro Maeda, Hiroshima (JP); Shigeyuki Kojima, Hiroshima (JP)

(73) Assignee: DELTA TOOLING CO., LTD., Hiroshima-shi (JP)

(*) Notice: Subject to any disclaimer, the term of this patent is extended or adjusted under 35 U.S.C. 154(b) by 961 days.

(21) Appl. No.: 13/321,367

(22) PCT Filed: May 18, 2010

(86) PCT No.: PCT/JP2010/058363
§ 371 (c)(1),
(2), (4) Date: Feb. 1, 2012

(87) PCT Pub. No.: WO2010/134525
PCT Pub. Date: Nov. 25, 2010

(65) Prior Publication Data
US 2012/0130261 A1   May 24, 2012

(30) Foreign Application Priority Data
May 19, 2009   (JP) .................. 2009-120849

(51) Int. Cl.
*A61B 5/024* (2006.01)
*A61B 5/00* (2006.01)
*A61B 5/11* (2006.01)

(52) U.S. Cl.
CPC ........... *A61B 5/6892* (2013.01); *A61B 5/02444* (2013.01); *A61B 5/4845* (2013.01);
(Continued)

(58) Field of Classification Search
CPC .... A61B 5/024; A61B 5/02416; A61B 5/026; A61B 5/0261; A61B 5/0263; A61B 5/0295; A61B 5/1102; A61B 5/4845; A61B 5/7235; B60W 2540/24
USPC ................................ 600/500–509
See application file for complete search history.

(56) References Cited

U.S. PATENT DOCUMENTS 7,195,596 B2 * 3/2007 Tsubata .................. 600/500
2004/0086060 A1 * 5/2004 Tsubata .................. 375/316
(Continued)

FOREIGN PATENT DOCUMENTS

JP   2004 344612   12/2004
JP   2004 344613   12/2004
(Continued)

OTHER PUBLICATIONS

Fujita, E., et al., "Development of simplified appraisal method of fatigue on sitting for extended periods by the data of finger plethysmogram," Japan Ergonomics Society, Ningen Kogaku, vol. 40, No. 5, pp. 254-263, (Oct. 15, 2004) (with English abstract).
(Continued)

*Primary Examiner* — Navin Natnithithadha
*Assistant Examiner* — Meredith Weare
(74) *Attorney, Agent, or Firm* — Oblon, McClelland, Maier & Neustadt, L.L.P.

(57) ABSTRACT

Determination about presence/absence of alcohol in the body is made accurately.
A frequency dynamic information processing means 610 which obtains a tendency of time-series fluctuation regarding a frequency of a pulse wave of a back portion of a person detected by an air pack and an alcohol-drinking determining means 650 which determines an alcohol-drinking state when a tendency of a time-series fluctuation regarding the frequency obtained by the frequency dynamic information processing means 610 is separated from a tendency of time-series fluctuation regarding the frequency at a non-drinking state are provided. Since determination about whether or not a person is in an alcohol-drinking state is made according to comparison with time-series fluctuation regarding the frequency at a non-drinking time, where the determination is made using not only frequency analysis of the frequency of a pulse wave changing according to the physical condition of the person but also the time-series fluctuation thereof, determination about presence/absence of alcohol drinking can be made more accurately as compared with the conventional method.

4 Claims, 30 Drawing Sheets

(52) U.S. Cl.
CPC ............. *A61B5/6887* (2013.01); *A61B 5/1102* (2013.01); *A61B 2503/22* (2013.01); *A61B 2562/168* (2013.01); *B60W 2540/24* (2013.01)

(56) References Cited

U.S. PATENT DOCUMENTS

| | | |
|---|---|---|
| 2004/0236235 A1 | 11/2004 | Fujita et al. |
| 2004/0260440 A1 | 12/2004 | Fujita et al. |
| 2007/0299636 A1 | 12/2007 | Fujita et al. |
| 2010/0117411 A1 | 5/2010 | Fujita et al. |
| 2010/0187881 A1* | 7/2010 | Fujita et al. ................ 297/284.3 |
| 2011/0251522 A1 | 10/2011 | Fujita et al. |

FOREIGN PATENT DOCUMENTS

| | | | |
|---|---|---|---|
| JP | 2007 090032 | 4/2007 | |
| JP | 2009 000493 | 1/2009 | |
| JP | 2009 219541 | 10/2009 | |
| WO | 2005 092193 | 10/2005 | |
| WO | WO 2008/143249 A1 * | 11/2008 | ............... A47C 7/28 |

OTHER PUBLICATIONS

Ochiai, N., et al., "The method for drinking detection by an automobile seat with the built-in seat sensor," Tokubetsugo, Dai 48 Kai Taikai Jimukyoku Meijo Daigaku Rikogakubu, Ningen Kogaku, vol. 43, pp. 192-193, (Jun. 2, 2007).

Kojima, S., et al., "Non-aggression Biological Signal Sensing System of Drink-driving," Society of Automotive Engineers of Japan Gakujutsu Koenkai Zensatsushu, Shadan Hojin Society of Automotive Engineers of Japan, No. 37, pp. 15-18, (May 23, 2007) (with English abstract).

Ochiai, N., et al., "The Application to Fatigue and Sleep Prediction, of The Signal of Biological Fluctuation Measured from Noninvasive Sensor," 39th Japan Ergonomics Society Chugoku and Shikoku Branch Convention, Collection of Literatures and Papers, Total 2 Pages, (Nov. 25, 2006).

Maeda, S., et al., "Trial Manufacture of Car Seat having a Non-Aggression Biological Signal Sensing Function," 39th Japan Ergonomics Society Chugoku and Shikoku Branch Convention, Collection of Literatures and Papers, Total 2 Pages, (Nov. 25, 2006).

International Search Report Issued Jun. 15, 2010 in PCT/JP10/058363 Filed May 18, 2010.

U.S. Appl. No. 13/266,188, filed Oct. 25, 2011, Fujita, et al.

* cited by examiner

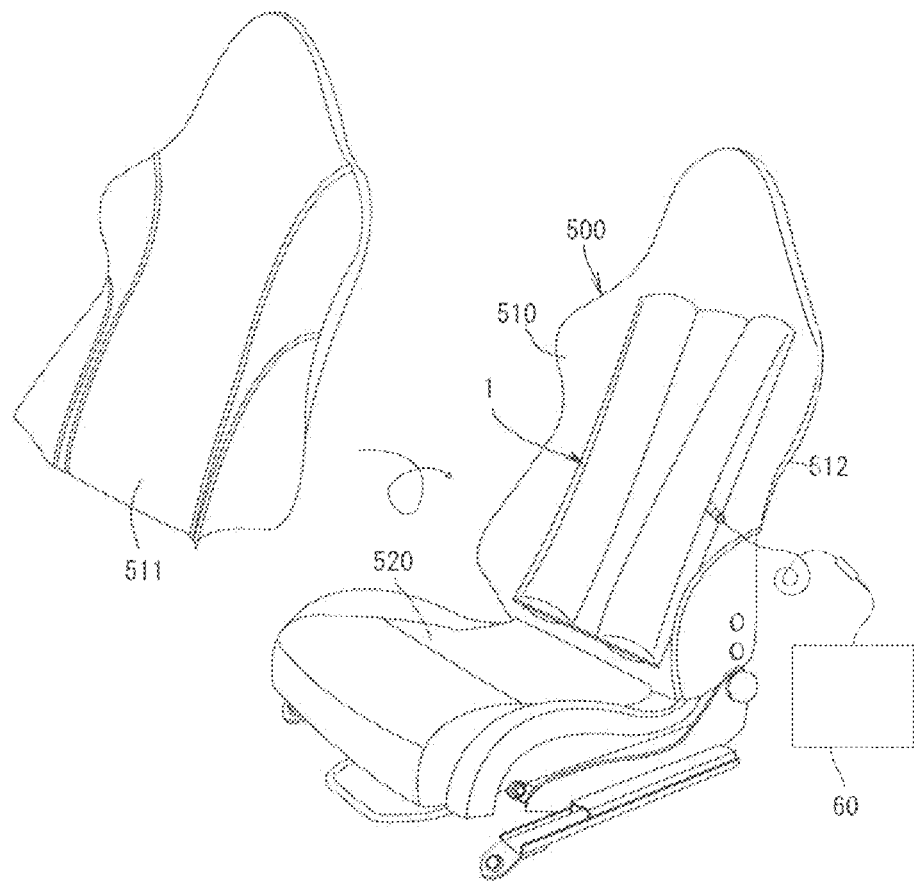

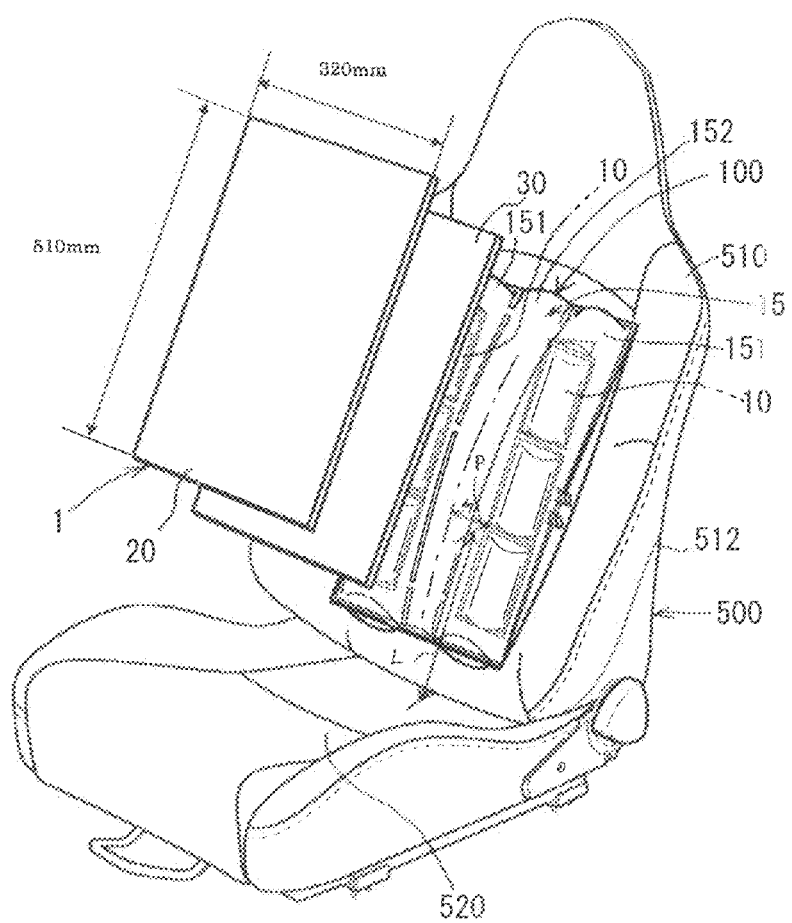

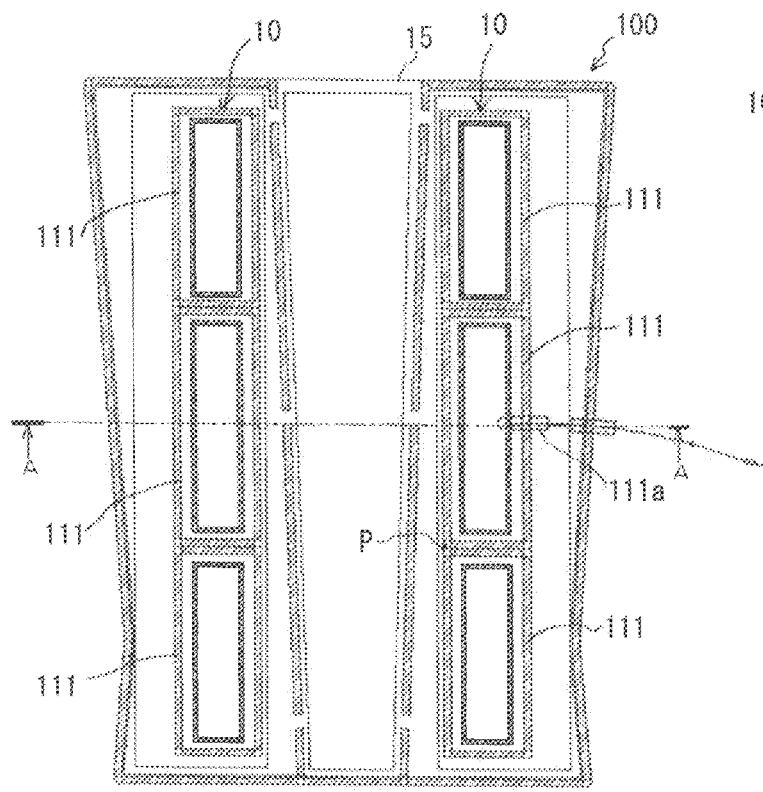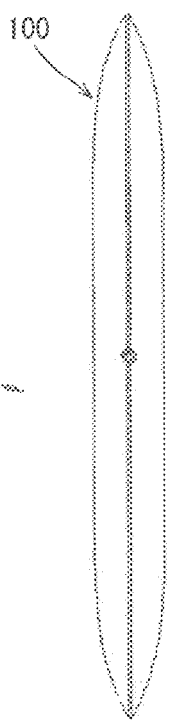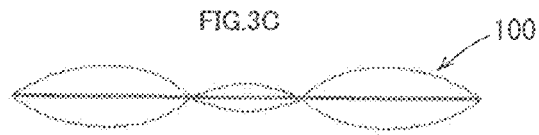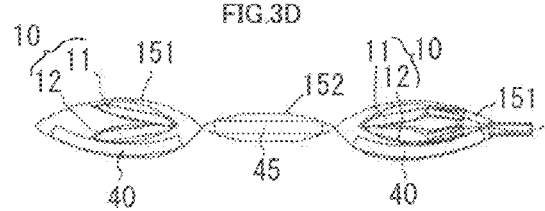

Pulse wave original waveform comparison
(Before drinking)

Finger photoplethysmogram analysis
(FFT analysis)

Air-pack pulse wave frequency analysis
(FFT analysis)

Before drinking

After drinking (1200-2400 sec)

After drinking (5400-6600 sec)

After drinking (9600-10800 sec)

Before drinking

After drinking (1200-2400 Sec)

Before drinking

After drinking (1200-2400 sec)

After drinking (5400-6600 sec.)

After drinking (9600-10800 sec.)

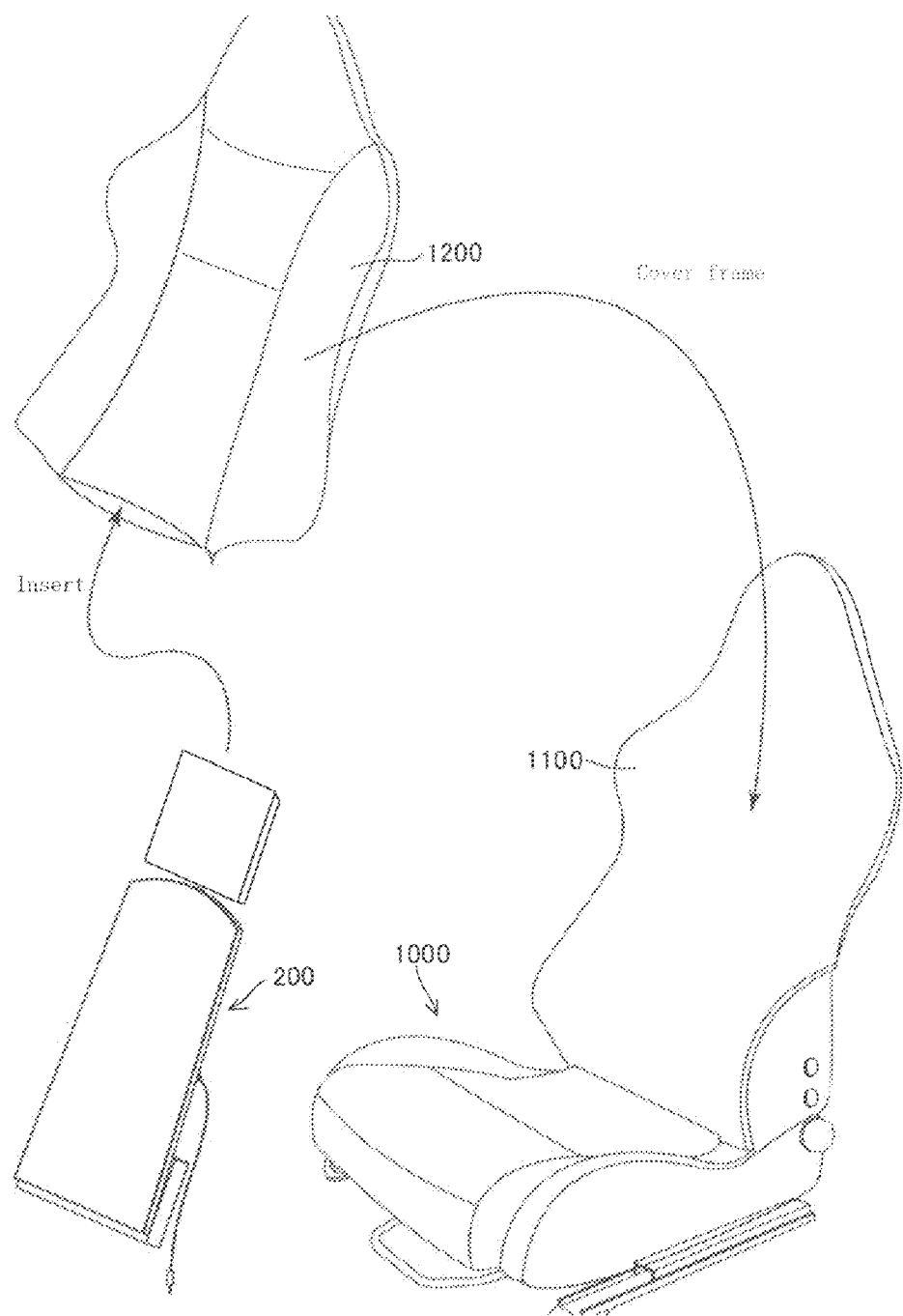

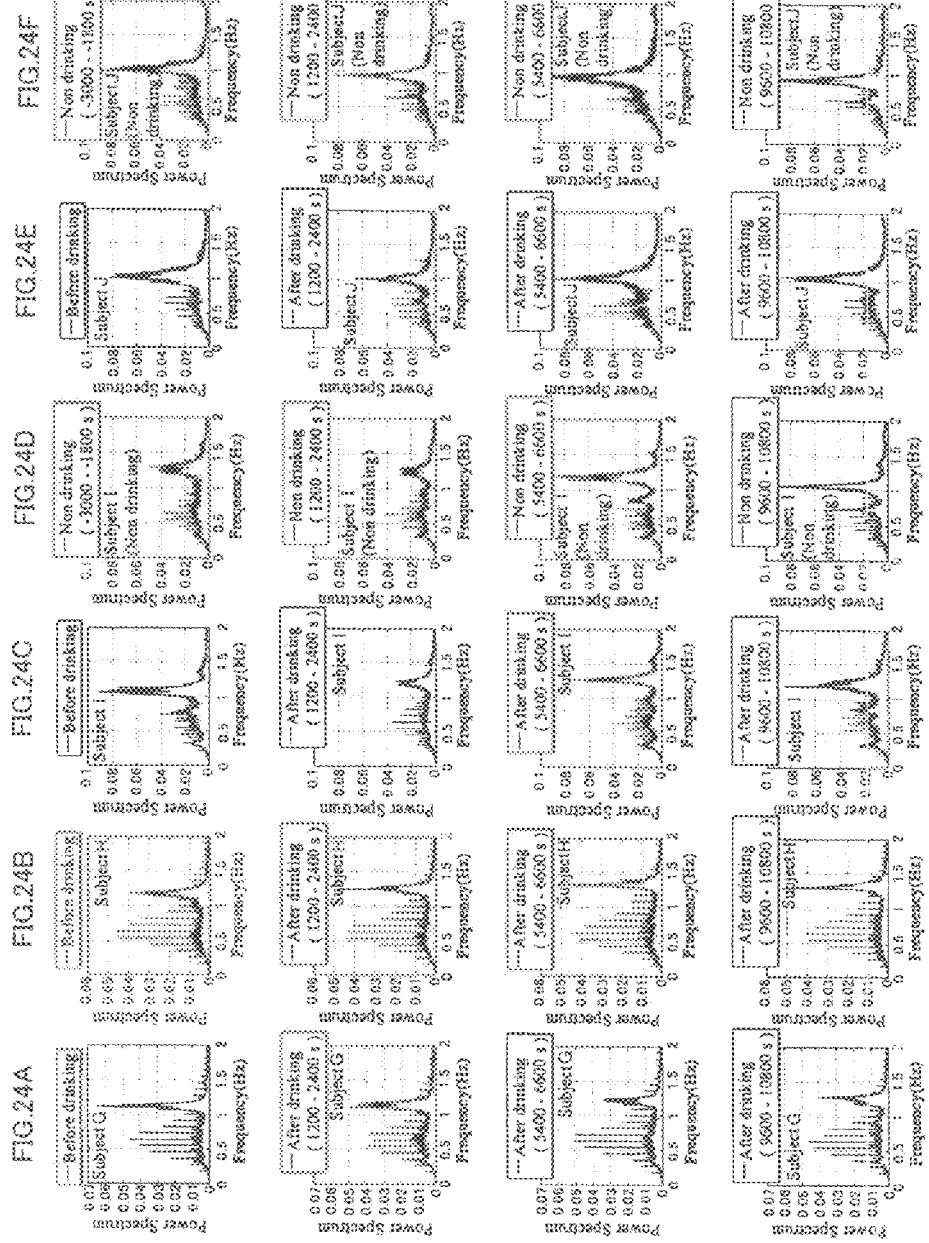

ALCOHOL-DRINKING DETECTING SYSTEM AND COMPUTER PROGRAM

TECHNICAL FIELD

The present invention relates to an alcohol-drinking detecting system and a computer program for detecting an alcohol-drinking state using a pulse wave of an artery of a person instead of a breath of a person.

BACKGROUND ART

As means for preventing drunken driving, it has been tried to mount an alcohol interlocking device on an automobile in recent years. In an alcohol-drinking detecting device utilizing a breath, however, there is such a concern that the device can be deceived by the breath of a fellow passenger.

On the other hand, the present applicant has disclosed a method for arranging a pressure sensor in a seat cushion section and obtaining and analyzing a pulse wave of a breech of a person to estimate the state of the person as a system which monitors a biological body state of a driver during driving in a non-invasive manner, for example, in Patent Literatures 1 to 3. Specifically, a maximum value and a minimum value of a time-series signal of a pulse wave are obtained by a smoothing differentiation method of Savitzky and Golay, respectively. The maximum value and the minimum value are obtained for each 5 seconds so that their mean values are obtained. Using a square of a difference between the respective mean values of the maximum values and the minimum values obtained as a power value, the power value is plotted for each 5 seconds so that a time-series waveform of the power value is produced. In order to read a global change of the power value from this time-series waveform, a slope of the power value regarding a certain time window Tw (180 seconds) is obtained by least-square method. Next, the slope regarding the next time window Tw is similarly calculated in an overlapped time TI (162 seconds) and the calculation results are plotted. A time-series waveform of the slope of the power value is obtained by repeating this calculation (moving calculation) sequentially. On the other hand, the maximum Lyapunov exponent is obtained by applying Chaos analysis to the time-series signal of the pulse wave, a maximum value is obtained by a smoothing differentiation method like the above, and a time-series waveform of a slope of the maximum Lyapunov exponent is obtained by conducting moving calculation. Then, the time-series waveform of the slope of the power value and the time-series waveform of the slope of the maximum Lyapunov exponent take phases opposite to each other, and a waveform having a large amplitude at a low frequency in the time-series waveform of the slope of the power value is determined as a characteristic signal indicating a sleep prediction and a point at which the amplitude has become small thereafter is determined as a sleep point.

Further, as Patent Literature 4, a system provided with an airbag (air pack) including a three-dimensional solid fabric inserted therein, where the air pack is disposed at a site corresponding to a waist portion of a person, an air pressure fluctuation in the air pack is measured, a biological signal of the person is detected from the time-series waveform of the air pressure fluctuation obtained, and the biological body state of the person is analyzed is disclosed. Further, in Non-Patent Literatures 1 and 2, trials for detecting a biological signal of a person by disposing an air pack sensor along a lumber iliocostal muscle are reported. A pulse wave near a lumber area shows a circulation fluctuation of blood flowing in a descending aorta according to a heartbeat, where a state change of a person corresponding to a heartbeat fluctuation can be captured more accurately in utilization of this aortic pulse wave than in utilizing the breech pulse wave disclosed in Patent Literatures 1 and 2.

The present applicant has reported that it is possible to determine presence/absence of alcohol in the body by further developing the techniques described in Patent Literatures 1 to 4 and Non-Patent Literatures 1 and 2 and performing frequency analysis of a pulse wave obtained from an air-pack sensor as Non-Patent Literature 3.

PRIOR ART LITERATURES

Patent Literature

Patent Literature 1: Japanese Patent Application Laid-Open No. 2004-344612
Patent Literature 2: Japanese Patent Application Laid-Open No. 2004-344613
Patent Literature 3: WO2005/092193A1
Patent Literature 4: Japanese Patent Application Laid-Open No. 2007-90032
Non-Patent Literature
Non-Patent Literature 1: "APPLICATION OF BIOLOGICAL WANDERING SIGNAL MEASURED BY NON-INVASIVE TYPE SENSOR TO FATIGUE AND SLEEP PREDICTION" by Naoki OCHIAI (and six others), 39th Japan Ergonomics Society Chugoku and Shikoku Branch convention, Collection of Literatures and Papers issued on Nov. 25, 2006 from Japan Ergonomics Society Chugoku and Shikoku Branch Secretariat
Non-Patent Literature 2: "TRIAL PRODUCTION OF VEHICLE SEAT HAVING NON-INVASIVE BIOLOGICAL SIGNAL SENSING FUNCTION" by Shinichiro MAEDA (and four others), 39th Japan Ergonomics Society Chugoku and Shikoku Branch Convention, Collection of Literatures and Papers issued on Nov. 25, 2006 from Japan Ergonomics Society Chugoku and Shikoku Branch Secretariat
Non-Patent Literature 3: "NON-INVASIVE SENSING SYSTEM FOR ALCOHOL-DRINKING STATE" By Shigeyuki KOJIMA (and ten others), Proceedings of Conference by SAE of Japan, No. 37-07, 15-18, issued May 23, 2007, Publication Office: Society of Automotive Engineers of Japan, Inc.

SUMMARY OF INVENTION

Technical Problem

As described above, Non-Patent Literature 3 shows that it is possible to perform frequency analysis of a time-series waveform of a pulse wave of an aorta of a dorsal region obtained from the air-pack sensor to make determination about presence/absence of alcohol in the body, but it is desirable that alcohol-drinking determination is made with higher accuracy.

The present invention has been made in view of the above circumstances and a problem to be solved by the invention is to provide an alcohol-drinking detecting system and a computer program which can further firmly detect whether or not a person has drunk alcohol.

Solution to Problem

In order to solve the above problem, the present invention is an alcohol-drinking detecting system which is provided with an alcohol-drinking analyzing and estimating section which analyzes a biological signal which can be obtained from a sensor which detects an air pressure fluctuation in an air pack disposed corresponding to a body of a person to estimate presence/absence of alcohol in the body, wherein the alcohol-drinking analyzing and estimating section comprises:

a frequency dynamic information processing means which obtains, from a time-series waveform of the biological signal, a time-series fluctuation regarding the frequency of the time series-waveform; and an alcohol-drinking state determining means which determines an alcohol-drinking state when a tendency of the time-series fluctuation regarding the frequency obtained from the frequency dynamic information processing means is separated from a tendency of the time-series fluctuation regarding the frequency at a non-drinking time.

Such a configuration can be adopted that the frequency dynamic information processing means includes a dominant frequency time-series waveform computing means which frequency-analyzes a time-series waveform in a predetermined time range of the biological signal to obtain a dominant frequency and obtains a dominant frequency time-series waveform, and the alcohol-drinking state determining means determines the alcohol-drinking state according to whether or not the dominant frequency time-series waveform is higher than that at a non-drinking time.

Such a configuration can be adopted that the frequency dynamic information processing means includes a dominant frequency time-series waveform computing means which frequency-analyzes a time-series waveform in a predetermined time range of the biological signal to obtain a dominant frequency and obtains a dominant frequency time-series waveform, and the alcohol-drinking state determining means determines the alcohol-drinking state according to whether or not a degree of fluctuation of a value of the dominant frequency of the dominant frequency time-series waveform in the predetermined time range is further expanded as compared with that at a non-drinking time.

Such a configuration can be adopted that the frequency dynamic information processing means includes a dominant frequency fluctuation time-series analyzing and computing means which performs moving calculation which obtains, for each of predetermined time windows set to the dominant frequency time-series waveform obtained by the dominant frequency time-series waveform computing means in a predetermined overlapping time, an average value of the dominant frequency to output a time-series change of the average value of the dominant frequency for the time window as a dominant frequency fluctuation time-series waveform, and the alcohol-drinking state determining means determines the alcohol-drinking state according to whether or not a base line position of the dominant frequency fluctuation time-series waveform is higher than that at a non-drinking time.

Such a configuration can be adopted that the frequency dynamic information processing means comprises a dominant frequency fluctuation time-series analyzing and computing means which performs moving calculation which obtains, for each of predetermined time windows set to the dominant frequency time-series waveform obtained by the dominant frequency time-series waveform computing means in a predetermined overlapping time, an average value of the dominant frequency to output a time-series change of the average value of the dominant frequency obtained for the time window as a dominant frequency fluctuation time-series waveform, and a dominant frequency slope time-series analyzing and computing means which performs moving calculation which obtains, for each of predetermined time windows set to the dominant frequency time-series waveform obtained by the dominant frequency time-series waveform computing means in a predetermined overlapping time, a slope of the dominant frequency to output a time-series change of the slope of the dominant frequency obtained for the time window as a dominant frequency slope time-series waveform; and the alcohol-drinking state determining means determines the alcohol-drinking state according to whether or not separation of a base line position of the dominant frequency fluctuation time-series waveform from a base line position of the dominant frequency slope time-series waveform obtained by the dominant frequency slope time-series analyzing and computing means is larger than that at a non-drinking time.

Such a configuration can be adopted that the frequency dynamic information processing means comprises a frequency computing means which obtains a time-series waveform of a frequency in the time-series waveform of the biological signal, and a frequency fluctuation time-series analyzing and computing means which performs moving calculation for obtaining, in a time-series waveform of a frequency of the biological signal obtained by the frequency computing means, an average value of the frequency for each of predetermined time windows set in a predetermined overlapping time to output a time-series change of the average value of the frequency obtained for each time window as a frequency fluctuation time-series waveform; and the alcohol-drinking state determining means determines the alcohol-drinking state according to whether or not a base line position of the frequency fluctuation time-series waveform is higher than that at a non-drinking time.

Such a configuration can be adopted that the frequency dynamic information processing means comprises a frequency computing means which obtains a time-series waveform of a frequency in the time-series waveform of the biological signal, and a frequency slope time-series analyzing and computing means which performs moving calculation for obtaining, in a time-series waveform of a frequency of the biological signal obtained by the frequency computing means, a slope of the frequency for each of predetermined time windows set in a predetermined overlapping time to output a time-series change of the slope of the frequency obtained for each time window as a frequency slope time-series waveform; and the alcohol-drinking state determining means determines the alcohol-drinking state according to whether or not, regarding a difference of an integral value of a positive slope and a difference of an integral value of a negative slope obtained by dividing the frequency slope time-series waveform into the positive slope and the negative slope to integrate the respective positive and negative slopes and comparing the integral values of the positive slope and the negative slope with those in a normal state before alcohol drinking, the difference of the integral value of the positive slope decreases to a predetermined difference or more and the difference of the integral value of the negative slope increases to a predetermined difference or more.

Such a configuration can be adopted that the frequency dynamic information processing means comprises a frequency computing means which obtains a time-series waveform of a frequency in the time-series waveform of the biological signal, a frequency fluctuation time-series analyzing and computing means which performs moving calculation for obtaining, in a time-series waveform of a frequency of the biological signal obtained by the frequency computing means, an average value of the frequency for each of predetermined time windows set in a predetermined overlapping time to output a time-series change of the average value of the frequency obtained for each time window as a frequency fluctuation time-series waveform, and a frequency slope time-series analyzing and computing means which performs moving calculation for obtaining, in the time-series waveform of the frequency of the biological signal obtained by the frequency computing means, a slope of the frequency for each of predetermined time windows set in a predetermined overlapping time to output a time-series change of the slope of the frequency obtained for each time window as a frequency slope time-series waveform; and the alcohol-drinking state determining means determines the alcohol-drinking state according to whether or not a base line position of the frequency fluctuation time-series waveform is higher than that at a non-drinking state and whether or not, regarding a difference of an integral value of a positive slope and a difference of an integral value of a negative slope obtained by dividing the frequency slope time-series waveform into the positive slope and the negative slope to integrate the respective positive and negative slopes and comparing the integral values of the positive slope and the negative slope with those in a normal state before alcohol drinking, the difference of the integral value of the positive slope decreases to a predetermined difference or more and the difference of the integral value of the negative slope increases to a predetermined difference or more.

The present invention provides a computer program configuring an alcohol-drinking analyzing and estimating process which analyzes a time-series signal of a biological signal obtained from a biological signal measuring device comprising an air pack which is disposed corresponding to a region where a pulse wave of a body of a person is detectable and a sensor which detects an air pressure fluctuation in the air pack to estimate presence/absence of alcohol in the body, the alcohol-drinking analyzing and estimating process being set in a storage section of an alcohol-drinking detecting system, wherein the alcohol-drinking analyzing and estimating process comprises:

a frequency dynamic information processing step of obtaining, from a time-series waveform of the biological signal, a time-series fluctuation regarding the frequency of the time series-waveform; and an alcohol-drinking state determining step of determining an alcohol-drinking state when a tendency of the time-series fluctuation regarding the frequency obtained by the frequency dynamic information processing step is separated from a tendency of a time-series fluctuation regarding the frequency at a non-drinking time.

Such a configuration can be adopted that the frequency dynamic information processing step includes a dominant frequency time-series waveform computing step of frequency-analyzing a time-series waveform in a predetermined time range of the biological signal to obtain a dominant frequency and obtains a dominant frequency time-series waveform, and the alcohol-drinking state determining step determines the alcohol-drinking state according to whether or not the dominant frequency time-series waveform is higher than that at a non-drinking time.

Such a configuration can be adopted that the frequency dynamic information processing step includes a dominant frequency time-series waveform computing step of frequency-analyzing a time-series waveform in a predetermined time range of the biological signal to obtain a dominant frequency and obtaining a dominant frequency time-series waveform, and the alcohol-drinking state determining step determines the alcohol-drinking state according to whether or not a degree of fluctuation of a value of the dominant frequency of the dominant frequency time-series waveform in a predetermined time range is further expanded as compared with that at a non-drinking time.

Such a configuration can be adopted that the frequency dynamic information processing step includes a dominant frequency fluctuation time-series analyzing and computing step of performing moving calculation which obtains, for each of predetermined time windows set to the dominant frequency time-series waveform obtained from the dominant frequency time-series waveform computing step in a predetermined overlapping time, an average value of the dominant frequency to output a time-series change of the average value of the dominant frequency for the time window as a dominant frequency fluctuation time-series waveform, and the alcohol-drinking state determining step determines the alcohol-drinking state according to whether or not a base line position of the dominant frequency fluctuation time-series waveform is higher than that at a non-drinking time.

Such a configuration can be adopted that the frequency dynamic information processing step comprises a dominant frequency fluctuation time-series analyzing and computing step of performing moving calculation which obtains, for each of predetermined time windows set to the dominant frequency time-series waveform obtained from the dominant frequency time-series waveform computing step in a predetermined overlapping time, an average value of the dominant frequency to output a time-series change of the average value of the dominant frequency obtained for the time window as a dominant frequency fluctuation time-series waveform, and a dominant frequency slope time-series analyzing and computing step of performing moving calculation which obtains, for each predetermined time window set to the dominant frequency time-series waveform obtained from the dominant frequency time-series waveform computing step in a predetermined overlapping time, a slope of the dominant frequency to output a time-series change of the slope of the dominant frequency obtained for the time window as a dominant frequency slope time-series waveform, and the alcohol-drinking state determining step determines the alcohol-drinking state according to whether or not separation of a base line position of the dominant frequency fluctuation time-series waveform from a base line position of the dominant frequency slope time-series waveform obtained from the dominant frequency slope time-series analyzing and computing step is larger than that at a non-drinking time.

Such a configuration can be adopted that the frequency dynamic information processing step comprises a frequency computing step of obtaining a time-series waveform of a frequency in the time-series waveform of the biological signal; and a frequency fluctuation time-series analyzing and computing step of performing moving calculation for obtaining, in a time-series waveform of a frequency of the biological signal obtained by the frequency computing step, an average value of the frequency for each of predetermined time windows set in a predetermined overlapping time to output a time-series change of the average value of the frequency obtained for each time window as a frequency fluctuation time-series waveform, and the alcohol-drinking state determining step determines the alcohol-drinking state according to whether or not a base line position of the frequency fluctuation time-series waveform is higher than that at a non-drinking time.

Such a configuration can be adopted that the frequency dynamic information processing step comprises:

a frequency computing step of obtaining a time-series waveform of a frequency in the time-series waveform of the biological signal; and a frequency slope time-series analyzing and computing step of performing moving calculation for obtaining, in a time-series waveform of a frequency of the biological signal obtained by the frequency computing step, a slope of the frequency for each of predetermined time windows set in a predetermined overlapping time to output a time-series change of the slope of the frequency obtained for each time window as a frequency slope time-series waveform, and the alcohol-drinking state determining step determines the alcohol-drinking state according to whether or not, regarding a difference of an integral value of a positive slope and a difference of an integral value of a negative slope obtained by dividing the frequency slope time-series waveform into the positive slope and the negative slope to integrate the respective positive and negative slopes and comparing the integral values of the positive slope and the negative slope with those in a normal state before alcohol drinking, the difference of the integral value of the positive slope decreases to a predetermined difference or more and the difference of the integral value of the negative slope increases to a predetermined difference or more.

Such a configuration can be adopted that the frequency dynamic information processing step comprises a frequency computing step of obtaining a time-series waveform of a frequency in the time-series waveform of the biological signal;

a frequency fluctuation time-series analyzing and computing step of performing moving calculation for obtaining, in a time-series waveform of a frequency of the biological signal obtained by the frequency computing step, an average value of the frequency for each of predetermined time windows set in a predetermined overlapping time to output a time-series change of the average value of the frequency obtained for each time window as a frequency fluctuation time-series waveform; and a frequency slope time-series analyzing and computing step of performing moving calculation for obtaining, in the time-series waveform of the frequency of the biological signal obtained by the frequency computing step, a slope of the frequency for each of predetermined time windows set in a predetermined overlapping time to output a time-series change of the average value of a slope of the frequency obtained for each time window as a frequency slope time-series waveform, and the alcohol-drinking state determining step determines the alcohol-drinking state according to whether or not a base line position of the frequency fluctuation time-series waveform is higher than that at a non-drinking state and whether or not, regarding a difference of an integral value of a positive slope and a difference of an integral value of a negative slope obtained by dividing the frequency slope time-series waveform into the positive slope and the negative slope to integrate the respective positive and negative slopes and comparing the integral values of the positive slope and the negative slope with those in a normal state before alcohol drinking, the difference of the integral value of the positive slope decreases to a predetermined difference or more and the difference of the integral value of the negative slope increases to a predetermined difference or more.

Advantageous Effects of Invention

According to the present invention, such a configuration is adopted that a tendency of a time-series fluctuation regarding a frequency of a biological signal detected from an upper body of a person by using a biological signal measuring device is obtained and whether or not the person is in an alcohol-drinking state is determined by comparison with a time-series fluctuation regarding a frequency at a non-drinking state. Since such a configuration is adopted that determination is made using not only a frequency analysis of a frequency of a biological signal changing according to a body condition of a person but also a time-series fluctuation of the frequency, presence/absence of alcohol in the body can be determined with accuracy higher than that in the conventional art.

BRIEF DESCRIPTION OF THE DRAWINGS

FIG. 1 is a view showing a state where a biological signal measuring device according to an embodiment of the present invention has been assembled into a seat;

FIG. 2 is a view showing the biological signal measuring device according to the embodiment in more detail;

FIGS. 3A to 3D are views showing an air-pack unit, FIG. 3A being a sectional view of the air-pack unit as viewed from the front, FIG. 3B being a side view thereof; and FIG. 3C being a bottom view thereof, and FIG. 3D being a sectional view thereof taken along line A-A;

FIG. 23 is a view for describing a process for assembling the biological signal measuring device shown in FIG. 21 or FIG. 22A or 22B into a seat;

FIG. 24 is diagrams showing aspects of fluctuations of breath-alcohol concentrations measured before and after measurements of aortic pulse waves of a test example 2;

DESCRIPTION OF EMBODIMENT

Hereinafter, embodiments of the present invention will be explained in detail with reference to the drawings. FIG. 1 is a view showing an exterior of an automobile seat 500 assembled with a biological signal measuring device 1 obtaining aortic pulse waves to be analyzed in an alcohol-drinking detecting system 60 according to this embodiment (biological signals involving motion of an atrium and fluctuation of an aorta detected from a dorsal region of an upper body of a person). As shown in this figure, the biological signal measuring device 1 is used in an assembled state thereof into a seatback section 510. Here, it is desirable that signals obtained by the biological signal measuring device 1 contain less noise signals except for biological signal components. In view of these circumstances, as described below, the biological signal measuring device 1 according to this embodiment has been applied with ingenuity which can reduce noise signals involved in sensor output signals themselves even under a vibration environment such as in a moving automobile.

Figure 4:
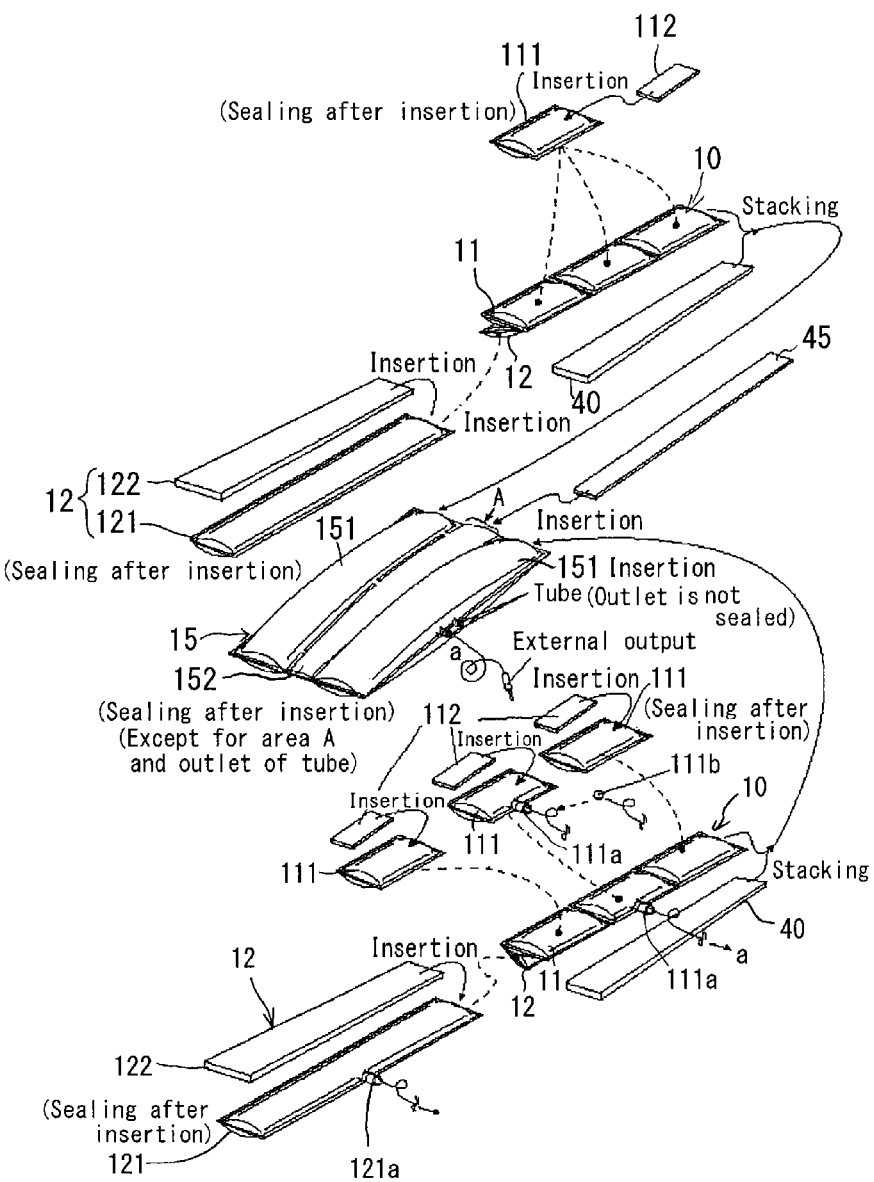
FIG. 4 is an exploded perspective view of the air-pack unit.
Figure 5A:
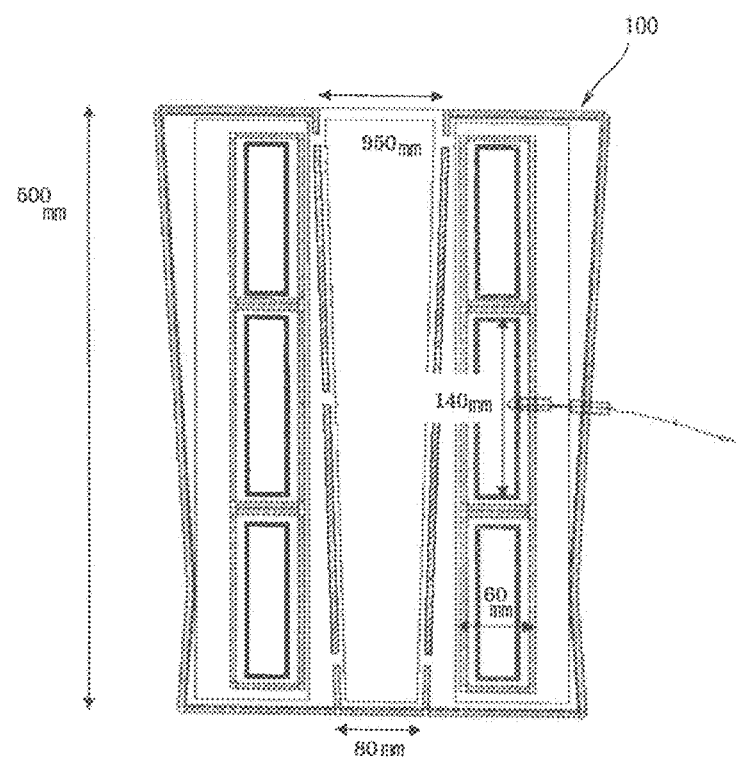
FIGS. 5A and 5B are views for describing a size of an air-pack unit used in a test example.
Figure 5B:
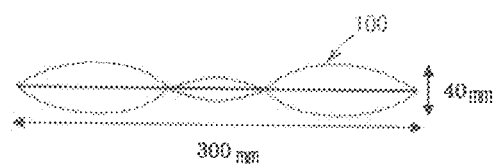

The biological signal measuring device 1 is configured to include an air-pack unit 100, a first elastic member 20 made of expanded resin beads, and a second elastic member 30 made of expanded resin beads. The air-pack unit 100 is configured to include a receiving body 15 and two air packs 10 received in this receiving body 15. As shown in FIGS. 3 and 4, the air packs 10 are each configured by stacking a surface side air pack 11 and a back surface side air pack 12, and they are disposed on the right and the left sides of the receiving body 15, respectively. The surface side air pack 11 is formed such that it comprises three small airbags 111 connected in series in a vertical direction, while air communication among these small airbags 111 is prevented. Three-dimensional solid knitted fabrics 112 serving as resilience-imparting members are disposed within the respective small airbags 111.

The back surface side air pack 12 is configured to include a large airbag 121 with the same length as the entire length of the surface side air pack comprising three small airbags 111 connected in series and a three-dimensional solid knitted fabric 122 serving as a resilience-imparting member and received in the large airbag 121 (see FIG. 4). The surface side air pack 11 and the back surface side air pack 12 are used, after they are joined to each other at their one edges positioned along their longitudinal directions and they are folded about the joined side edges to be stacked on each other (see FIG. 3D and FIG. 4).

In this embodiment, air packs 10 obtained by stacking the surface side air pack 11 and the back surface side air pack 12 mutually in this manner are arranged on the right side and the left side. The arrangement of the respective air packs 10 on the right side and the left side makes contact of the seatback section to the back of a person sitting on the seat bilaterally even, so that the person does not feel uncomfortable. Further, a sensor mounting tube 111a is provided to one of the small airbags 111 configuring one of the right and left surface side air packs 11, 11, and a sensor 111b which measures air pressure fluctuation is fixed inside the small airbag 111. Incidentally, the sensor mounting tube 111a is sealed. Though the sensor may be disposed in the large airbag 121 configuring the back surface side air pack 12, if the sensor is provided in an airbag having a large volume, there is such a possibility that, air pressure fluctuation due to a biological signal is absorbed by the airbag, so that it is preferred that the sensor is provided in the small airbag 111. As shown in FIG. 4, however, such a configuration can be adopted that the mounting tube 121a is preliminarily provided to the large airbag 121 and the sensor is arranged at the site of the mounting tube 121a, so that a result obtained by measuring air pressure fluctuation in the large airbag 121 can be utilized for verification of the measurement result of the small airbag 111 as necessary. In order to cause the small airbag 111 to respond to air pressure fluctuation due to such a biological signal susceptibly, it is preferred that the size of the small airbag 111 has a width of 40 to 100 mm and a length of 120 to 200 mm. A material for the small airbag 111 is not limited, but the small airbag 111 may be formed of a sheet made of, for example, polyurethane elastomer (for example, Product Number "DUS605-CDR" produced by Sheedom Co., Ltd.). As the sensor 111b, one which can measure air pressure within the small airbag 111 can be used, for example, a capacitive microphone sensor can be used.

As the size of the large airbag 121 and the entire size of the three small airbags 111 connected in series, it is preferred that the width and the entire length fall within a range of 40 to 100 mm and a range of 400 to 600 mm when these airbags 121 and 111 are used in the seatback section 510 of the automobile seat 500. When the length is short, a person sitting on the seat feels uncomfortable only at a portion of the seat positioned near his/her lumber area in the seatback section 510, so that it is preferred that the length is set to 400 mm or more and the airbags accommodate the entire back of the person sitting on the seat as much as possible.

In this embodiment, the sensor 111b which detects air pressure fluctuation is provided in a central small airbag 111 of the surface side air pack 11 configuring the air pack 10 arranged on the left side of the person sitting on the seat. The position of the small airbag 111 corresponds to a region where biological signals (aortic pulse waves) involved in motion of an atrium and fluctuation of an aorta (especially, "descending aorta") obtained from the dorsal region of the person are detectable. The region where the aortic pulse waves are detectable is not uniform due to the frame of a person sitting on the seat, but, as a result of measuring 20 subjects of various build from a 158-centimeter-tall Japanese woman to a 185-centimeter-tall Japanese man, the aortic pulse waves regarding all the subjects could be detected when an intersecting portion P (see FIG. 2 and FIG. 3) of a side edge of the small airbag 111 (having a width of 60 mm and a length of 160 mm) positioned nearer to the center of the seatback section 510 and a lower edge thereof was set such that a length L from an upper face of the seat cushion section 520 along a surface of the seatback section 510 was 220 mm and a distance M from the center of the seatback section 510 was 80 mm. When the size of the small airbag 111 is set such that its width is in a range of 40 to 100 mm and its length is in a range of 120 to 200 mm, it is preferred that the position of the intersecting portion P is set such that the length from the upper face of the seat cushion section 520 along the surface of seatback section 510 is in a range of 150 to 280 mm and the distance from the center of the seatback section 510 is in a range of 60 to 120 mm.

It is preferred that the above-described two air packs 10 are unitized such that they can be easily set at predetermined positions in the seatback section 510. Therefore, it is preferred that an air-pack unit 100 obtained by loading the air packs 10 into a receiving body 15 such as shown in FIG. 2 to FIG. 4 is configured. The receiving body 15 has bag-shaped air pack receiving portions 151 receiving the air pack 10 on both sides and, and it has a connecting portion 152 between two air pack receiving portions 151.

The air packs 10 are inserted into two air pack receiving portions 151, respectively. It is also preferred that a three-dimensional solid knitted fabric 40 with approximately the same size as the air pack 10 is inserted into the air pack receiving portion 151 so as to be positioned on a back face of the back surface side air pack 12 of the air pack 10 in a stacking state (see FIG. 3D). By arranging the three-dimensional solid knitted fabric 40, the air pack 10 is supported in a so-called floating manner by the three-dimensional solid knitted fabric 40, so that transmission of external vibrations from the seatback section 510 becomes difficult. That is, by arranging the three-dimensional solid knitted fabric 40, a spring-mass-damper system with a low spring constant is produced within the air pack from piles of the three-dimensional solid knitted fabric 40 and fluctuation of air pressure at an inputting time of high-frequency external vibrations with small amplitude. Then, the spring-mass-damper system serves as filters to low-frequency and high-frequency inputs (a low-pass filter and a high-pass filter) in the air pack 10 housing the three-dimensional solid knitted fabric 40 therein to damp the external vibrations.

The connecting portion 152 may be a member which can support two air packs 151 spaced from each other by a predetermined distance, and it is formed to have a width of about 60 to 120 mm. It is preferred that the connecting portion 152 is formed in a bag shape, so that a three-dimensional solid knitted fabric 45 is inserted therein (see FIG. 3D and FIG. 4). Thereby, vibrations inputted through the connecting portion 152 can also be removed effectively by inserting the three-dimensional solid knitted fabric 45 into the connecting portion 152, so that transmission of external vibrations to the air pack 10 provided with the sensor 111b can be suppressed.

Incidentally, as described above, the small airbag 111 can be formed of a sheet made of, for example, polyurethane elastomer (for example, Product Number "DUS605-CDR" produced by Sheedom Co., Ltd.), but it is preferred that the large airbag 121 forming the back surface side air pack 12 and the receiving body 15 are also made of the same material as that for the small airbag 111. The respective three-dimensional solid knitted fabrics loaded into the small airbags 111, the large airbag 121, the air pack receiving portion 151, and the connecting portion 152 are knitted fabrics having a solid three-dimensional structure having a pair of ground knitted fabrics arranged so as to be spaced from each other and many connecting strands reciprocating between the pair of ground knitted fabrics to connect both the ground knitted fabrics, as disclosed in Japanese Patent Application Laid-Open No. 2002-331603.

One of the ground knitted fabrics is formed of, for example, a flat knitted fabric texture (fine mesh) continuous both in a wale direction and in a course direction from strands obtained by twisting monofilaments, while the other ground knitted fabric is formed of, for example, a knitted stitch structure having a honeycomb shape (hexagonal shape) meshes from strands obtained by twisting monofilaments. Of course, the knitted fabric texture is arbitrary, and a knitted fabric texture other than the fine mesh texture or the honeycomb shape can be adopted, and any combination of knitted fabric textures such as adoption of the fine mesh texture in both the ground knitted fabrics can be adopted in both the ground knitted fabrics. The connecting strands are knitted between the two ground knitted fabrics such that one of the ground knitted fabrics and the other are kept away from each other by a predetermined distance. As such a three-dimensional solid knitted fabric, for example, materials described below can be used. Incidentally, the respective three-dimensional solid knitted fabrics can also be used in a state that a plurality of three-dimensional solid knitted fabrics has been stacked one on another as necessary.

(1) Product Number: 49076D (Produced by Suminoe Textile Co., Ltd.) Material:

Surface side ground knitted fabric . . . twisted yarn of polyethylene terephthalate fiber false-twisted yarn of 300 decitex/288 f and polyethylene terephthalate fiber false-twisted yarn of 700 decitex/192 f Back surface side ground knitted fabric . . . combination of polyethylene terephthalate fiber false-twisted yarn of 450 decitex/108 f and poly-trimethylene telephthalate monofilament of 350 decitex/1 f Connecting strand . . . poly-trimethylene terephthalate monofilament of 350 decitex/1 f (2) Product Number: 49011D (Produced by Suminoe Textile Co., Ltd.) Material:

Ground knitted fabric (warp) . . . polyethylene terephthalate fiber false-twisted yarn of 600 decitex/192 f Ground knitted fabric (weft) . . . polyethylene terephthalate fiber false-twisted yarn of 300 decitex/72 f Connecting strand . . . polyethylene terephthalate monofilament of 800 decitex/1 f (3) Product Number: 49013D (Produced by Suminoe Textile Co., Ltd.) Material:

Surface side ground knitted fabric . . . twisted yarn of two polyethylene terephthalate fiber false-twisted yarns of 450 decitex/108 f Back surface side ground knitted fabric . . . twisted yarn of two polyethylene terephthalate fiber false-twisted yarns of 450 decitex/108 f Connecting strand . . . poly-trimethylene terephthalate monofilament of 350 decitex/1 f (4) Product Number: 69030D (Produced by Suminoe Textile Co., Ltd.) Material:

Surface side ground knitted fabric . . . twisted yarn of two polyethylene terephthalate fiber false-twisted yarns of 450 decitex/144 f Back side surface ground knitted fabric . . . combination of polyethylene terephthalate fiber false-twisted yarn of 450 decitex/144 f and poly-trimethylene telephthalate monofilament of 350 decitex/1 f Connecting strand . . . poly-trimethylene terephthalate monofilament of 350 decitex/1 f (5) Product Number Produced by Asahi Kasei Fibers Corporation: T24053AY5-1S The first elastic member made of expanded rein beads 20 and the second elastic member made of expanded resin beads 30 are disposed between a skin member of the seatback section 510 and the receiving body 15 (air-pack unit 100) which has received the air packs 10 therein. They have a length corresponding to the entire length of two air packs 10 and they have a width corresponding to a length between top portions of two air packs 10. Therefore, it is preferred that members having such a size that a length is in a range of 400 to 600 mm and a width is in a range of about 250 to 350 mm are used. Thereby, since two air packs 10 are covered with these members, undulation feeling due to the two air packs 10 is reduced.

The first elastic member made of expanded resin beads 20 is composed of an expanded bead body formed in a flat-plate shape and a covering material caused to adhere to an outer face of the expanded bead body. As the expanded bead body, an expanded formation body obtained by a bead method of resin containing at least one of polystyrene, polypropylene, and polyethylene is used. Incidentally, an expansion ratio is set arbitrarily and it is not limited. The covering material is caused to adhere to an outer face of the expanded bead body by adhesive, and it is a material having a high extension percentage and a high recovery rate, so that an elastic fiber nonwoven fabric whose extension percentage is at least 200% and whose recovery rate at 100% extension time is 80% is preferably used. For example, a nonwoven fabric where thermoplastic elastomer elastic fibers have been caused to adhere to one another in a melting manner, which is disclosed in Japanese Patent Application Laid-Open NO. 2007-92217, can be used. Specifically, Trade Name "Espansione" produced by KB SEIREN, LTD. can be used.

The second elastic member made of expanded resin beads 30 is configured to have an expanded bead body like the first elastic member made of expanded resin beads 20, but as a covering material for covering an outer face of the expanded bead body, a material with a retractility smaller than that of the elastic fiber nonwoven fabric used in the first elastic member made of expanded resin beads 20, for example, a nonwoven fabric made of thermoplastic polyester is used. Specifically, a biaxial fabric (longitudinal: 20/inch, horizontal: 20/inch) formed from polyethylene naphthalate (PEN) fibers (1100 dtex) produced by TEIJIN LIMITED can be used.

The order of stacking the first elastic member made of expanded resin beads 20 and the second elastic member made of expanded resin beads 30 is not limited, but it is preferred that the first elastic member made of expanded resin beads 20 having a higher elasticity is disposed on a side closer to the skin member 511 of the seatback section 510. Further, the expanded bead body constituting the first and second elastic member made of expanded resin beads 20 and 30 is set to have a thickness of about 5 to 6 mm, and formation thereof is achieved by causing a nonwoven fabric made of the above-described elastic fiber nonwoven fabric or thermoplastic polyester having a thickness of about 1 mm or less to adhere to an outer face thereof. Incidentally, in the embodiment, polyester films such as a PEN film are caused to adhere to a face of the first elastic member made of expanded resin beads 20 opposed to the skin member 511 and a face of the second elastic member made of expanded resin beads 30 opposed to the air-pack unit 100, respectively. Thereby, transmissibility of a biological signal is improved.

In the embodiment, the seatback section 510 of the seat 500 configuring a human body supporting means is provided with the skin member 511 and a cushion supporting member 512 disposed on a back surface side of the skin member 511, and the receiving body 15 (air-pack unit 100) holding the air packs 10 and the first and second elastic members made of expanded resin beads 20 and 30 are assembled between the skin member 511 and the cushion supporting member 512. At this time, the receiving body 15 (air-pack unit 100) holding the air packs 10 is first disposed on the side of the cushion supporting member 512, the second elastic member made of expanded resin beads 30 is disposed on a surface side of the receiving body 15, and after the first elastic member made of expanded resin beads 20 is further disposed on a surface side of the second elastic member made of expanded resin beads 30, these members are covered with the skin member 511. Incidentally, the cushion supporting member 512 can be formed by stretching a three-dimensional solid knitted fabric between rear end edges of a pair of right and left side frames of the seatback section 510 or can be formed of a synthetic resin plate. The skin member 511 can be provided by stretching, for example, a three-dimensional solid knitted fabric, an artificial leather, a leather, or a laminated body of these members between front edges of the pair of right and left side frames.

In this embodiment, thus, since the configuration where the first elastic member made of expanded resin beads 20 and the second elastic member made of expanded resin beads 30 which have predetermined sizes are disposed on the back surface side of the skin member 511 in a stacking state and the receiving body 15 (air-pack unit 100) holding the a pair of right and left air packs 10 is further disposed behind them is adopted, a person sitting on the seat is prevented from feeling undulation of the air packs 10 on his/her back, and sitting feeling is improved though the configuration having the air packs 10 for measuring biological signals is adopted.

Figure 6:
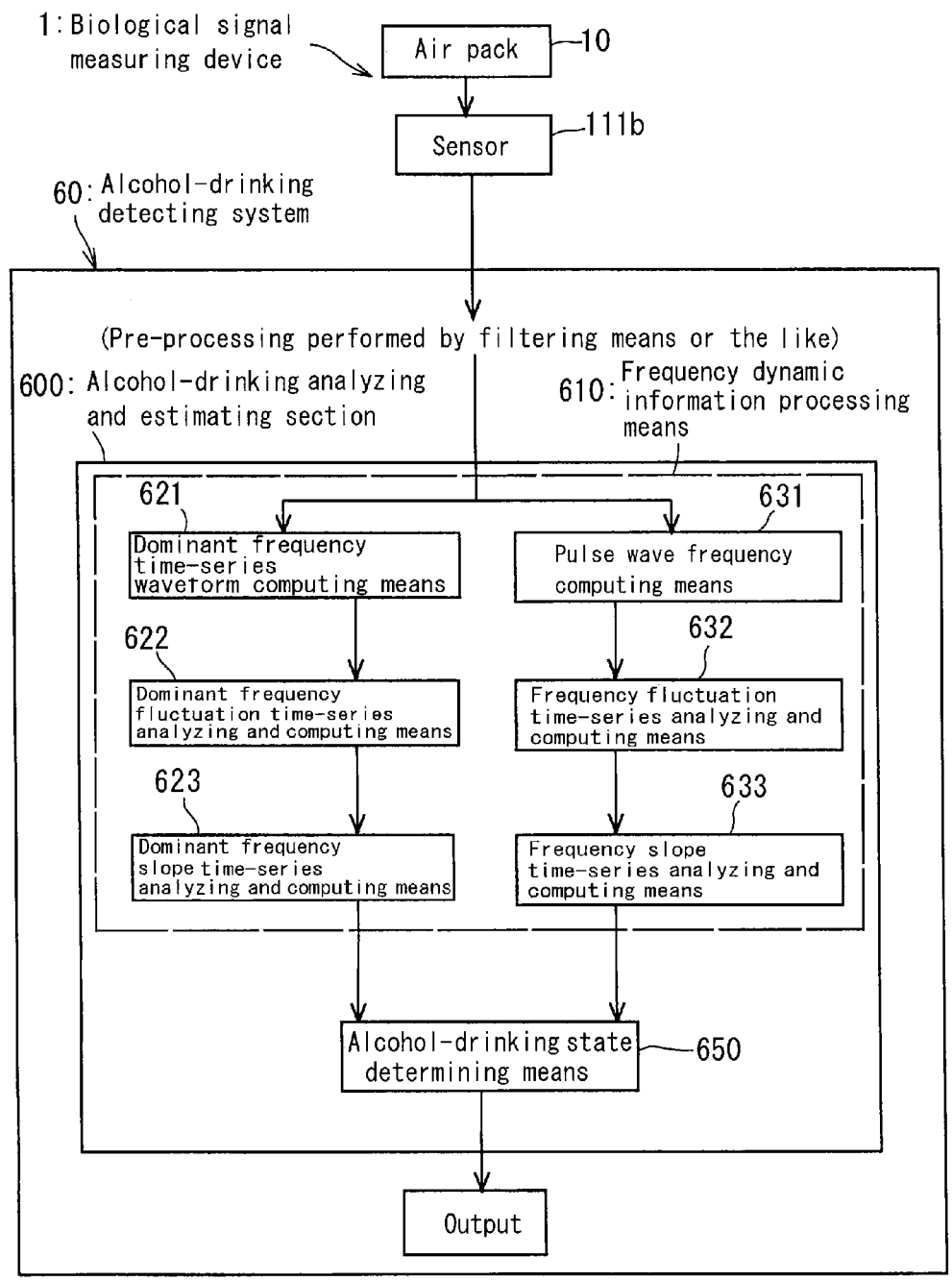
FIG. 6 is a diagram showing a configuration of a biological body state analyzing device.

Next, the configuration of the alcohol-drinking detecting system 60 will be described with reference to FIG. 6. The alcohol-drinking detecting system 60 is assembled with an alcohol-drinking analyzing and estimating section 600 which analyzes a time-series waveform of a aortic pulse wave (hereinafter, called "air-pack pulse wave" in some cases) which is a biological signal detected by the biological signal measuring device 1 to estimate presence/absence of alcohol in the body. Incidentally, since the biological signal measuring device 1 used in this embodiment has been applied with measure against noise, as described above, mixing of noise into detected signals is reduced, but such a case where noise other than aortic pulse waves is contained in detected signals especially under a dynamic environment such as during automobile driving often occurs. In such a case, therefore, it is preferred that, as pre-processing performed before processing is performed in the alcohol-drinking analyzing and estimating section 600, processing such as filtrating a detected signal at a predetermined frequency containing a aortic pulse wave is performed, and the pre-processed detected signal is used as a time-series waveform of the aortic pulse wave (air-pack pulse wave).

In this embodiment, the alcohol-drinking analyzing and estimating section 600 is composed of a computer program set in a storage section of the alcohol-drinking detecting system 60. That is, the alcohol-drinking analyzing and estimating section 600 is composed of a frequency dynamic information processing means 610 which obtains, from a time-series waveform of an air-pack pulse wave obtained from the biological signal measuring device 1, a time-series fluctuation regarding the frequency of the time-series waveform of the air-pack pulse wave, and an alcohol-drinking state determining means 650 which determines as an alcohol-drinking state a case where a tendency of a time-series fluctuation regarding the frequency obtained by the frequency dynamic information processing means 610 is separated from a tendency of a time-series fluctuation regarding a frequency at a non-drinking time.

The frequency dynamic information processing means 610 is configured to further include a dominant frequency time-series waveform computing means 621, a dominant frequency fluctuation time-series analyzing and computing means 622, a dominant frequency slope time-series analyzing and computing means 623, a frequency computing means 631, a frequency fluctuation time-series waveform analyzing and computing means 632, and a frequency slope time-series analyzing and computing means 633.

Incidentally, these computer programs can be provided in a state stored in such a recording medium as a flexible disk, a hard disk, a CD-ROM, an MO (magnetooptic disk), or a DVD-ROM, and it may also be transmitted through a communication line.

Figure 11:
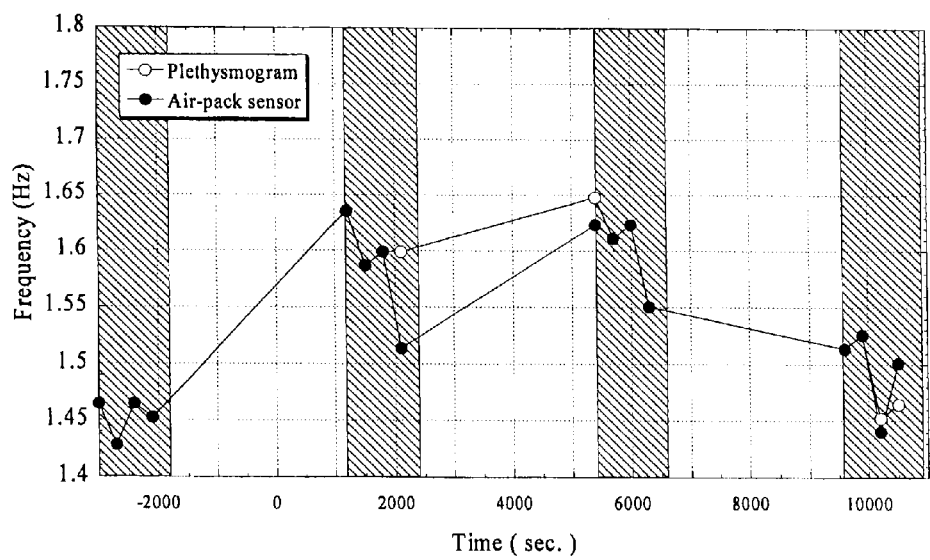
FIG. 11 is a diagram showing dominant frequency time-series waveforms of a finger photoplethysmogram and an air-pack pulse wave of the subject A obtained in time windows of 300 seconds.
Figure 12:
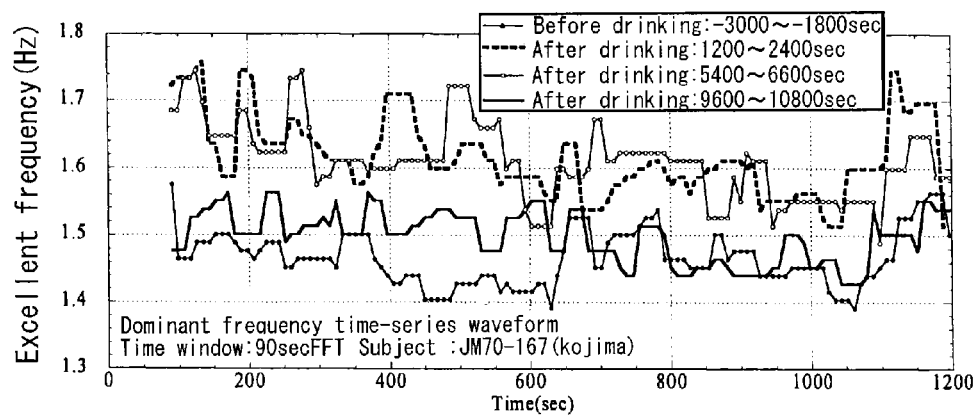
FIG. 12 is a diagram showing, in detail, dominant frequency (excellent frequency) time-series waveforms of air-pack pulse waves of the subject A obtained in time-windows of 90 seconds in a period from −3000 to −1800 second before alcohol drinking, in a period from 1200 to 2400 second after alcohol drinking, and in a period from 5400 to 6000 second after alcohol drinking, and in a period from 9600 to 10800 second after alcohol drinking.
Figure 13:
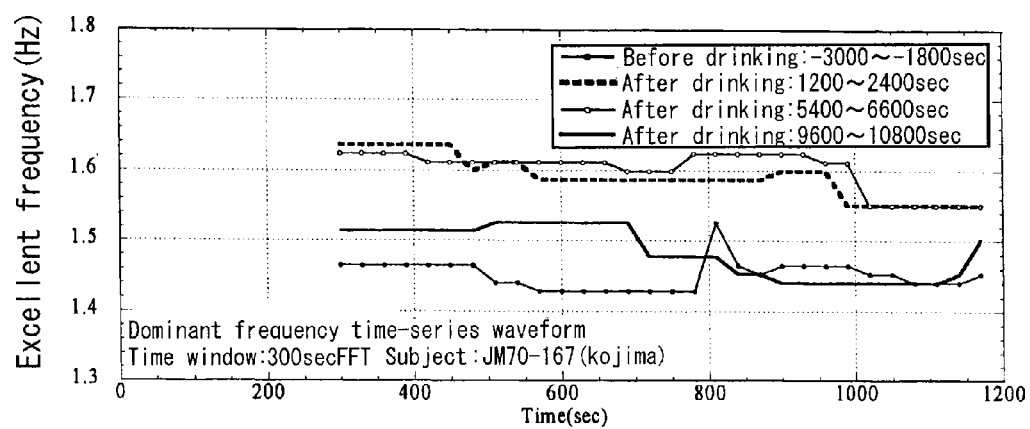
FIG. 13 is a diagram showing, in detail, dominant frequency time-series waveforms of air-pack pulse waves of the subject A obtained in time windows of 300 seconds in a period from −3000 to −1800 second before alcohol drinking, in a period from 1200 to 2400 second after alcohol drinking, and in a period from 5400 to 6000 second after alcohol drinking, and in a period from 9600 to 10800 second after alcohol drinking.

The dominant frequency time-series waveform computing means 621 frequency-analyzes a time-series waveform in a predetermined time range of an air-pack pulse wave to obtain a dominant frequency, thereby obtaining a dominant frequency time-series waveform. The dominant frequency time-series waveform is obtained by frequency-analyzing a time-series waveform of an air-pack pulse wave in a time window such as, for example, 90 seconds or 300 seconds. As shown in FIG. 11, such a configuration can be adopted that the dominant frequency time-series waveform is obtained for each time window of 300 seconds without including overlapping (namely, in the case shown in FIG. 11, dominant frequencies at four points are obtained in a measurement time of 20 minutes), but, as shown in FIG. 12 and FIG. 13, such a configuration can be adopted that, for example, time-windows of 90 seconds or time-windows of 300 seconds are set and a dominant frequencies are obtained for respective time windows while the time windows are overlapping with one another in a range of a time of 90% of the time windows. There is such an advantage that the tendency of transition of the dominant frequency is reflected in processing shown in FIG. 12 and FIG. 13 more strongly than in the processing shown in FIG. 11.

Figure 7:
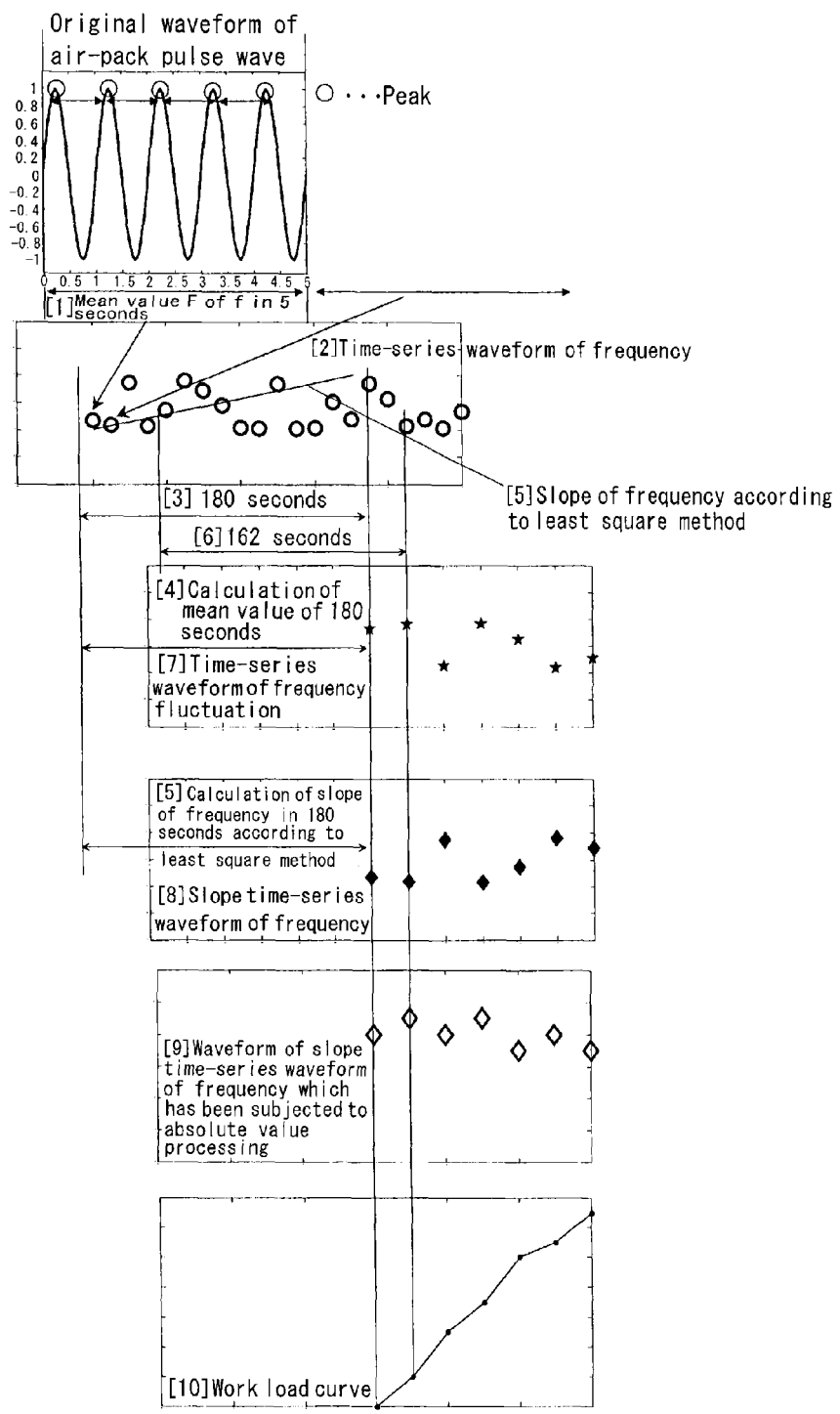
FIG. 7 is a diagram for describing a method for obtaining a frequency fluctuation time-series waveform, a base line of the frequency fluctuation time-series waveform, a frequency slope time-series waveform which is a slope time series of a frequency fluctuation, and an integral curve using a peak value of a biological signal (heartbeat fluctuation) detected by the biological signal measuring device.

The dominant frequency fluctuation time-series analyzing and computing means 622 sets a time window having a predetermined time width (preferably, 180 seconds) to the dominant frequency time-series waveform obtained by the dominant frequency time-series waveform computing means 621 to obtain an average value of the frequency (see Steps [3] and [4] in FIG. 7). Next, moving calculation for obtaining an average value of the dominant frequency calculated for each predetermined time window (preferably, 180 seconds) set in a predetermined overlapping time (preferably 162 seconds) for the time is performed and the average value is plotted. Then, a time-series change of the average value of the frequency plotted for each time window is outputted as a dominant frequency fluctuation time-series waveform (see Step [7] in FIG. 7).

The dominant frequency slope time-series analyzing and computing means 623 performs moving calculation for obtaining a slope of the dominant frequency for each predetermined time window set to the dominant frequency time-series waveform obtained by the dominant frequency time-series waveform computing means 621 in a predetermined overlapping time to output a time-series change of a slope of the dominant frequency obtained for each time window as a dominant frequency slope time-series waveform. Specifically, first of all, a slope of a frequency in a certain time window Tw1 is obtained by least square method and the slope is plotted (see Steps [3] and [5] in FIG. 7). Next, the next time window Tw2 is set in an overlapping time TI (Step [6] in FIG. 7) and a slope of a dominant frequency in this time window Tw2 is similarly obtained by least square method and the slope is plotted. This calculation (moving calculation) is repeated sequentially to output a time-series change of a slope of the dominant frequency of the air-pack pulse wave as a dominant frequency slope time-series waveform (see Step [8] in FIG. 7). Incidentally, it is preferred that the time width of the time window Tw is set to 180 seconds, and it is preferred that the overlapped time TI is set to 162 seconds. These values were selected as values at which a characteristic signal waveform which shows the state of a person emerged with the best sensitivity from sleep experiments performed while changing the time width of the time window Tw and the overlapped time TI variously, as shown in the above-described Patent Literature 3 (WO 2005/092193A1) of the present applicant.

The frequency computing means 631 obtains a time-series waveform of the frequency in the time-series waveform of the air-pack pulse wave obtained from the biological signal measuring device 1. Specifically, first of all, a maximum value (peak) is obtained by smoothing-differentiating the time-series waveform of the air-pack pulse wave. For example, the maximum value is obtained by a smoothing differentiation method of Savitzky and Golay. Next, the maximum value is obtained for each 5 seconds, a reciprocal of a time interval between the maximum values (peaks of a waveform on an upper side) of the time-series waveform contained in the 5 seconds is obtained as an individual frequency f, and a mean value of the individual frequencies f for the 5 seconds is adopted as a value of a frequency F for the 5 seconds (see Step [1] in FIG. 7). Then, a time-series waveform of the frequency is obtained by plotting the frequency F obtained for each 5 seconds (see Step [2] in FIG. 7).

The frequency fluctuation time-series analyzing and computing means 632 sets a time window having a predetermined time width (preferably, 180 seconds) in the time-series waveform of the frequency of the air-pack pulse wave obtained by the frequency computing means 631 (see Step [2] in FIG. 7) to obtain an average value of the frequency (see Steps [3] and [4] in FIG. 7). Next, moving calculation for obtaining an average value of the frequency of the air-pack pulse wave for each predetermined time window (preferably, 180 seconds) set in a predetermined overlapping time (preferably 162 seconds) is performed and the average value is plotted. Then, a time-series change of the average value of the frequency plotted for each time window is outputted as a frequency fluctuation time-series waveform (see Step [7] in FIG. 7).

The frequency time-series analyzing slope computing means 633 sets a time window having a predetermined time width from the time-series waveform of the frequency of the air-pack pulse wave obtained by the frequency computing means 631 and obtains a slope of the frequency of the air-pack pulse wave for each time window by least square method to output a time-series waveform of the slope. Specifically, first of all, a slope of a frequency in a certain time window Tw1 is obtained by least-square method and the slope is plotted (see Steps [3] and [5] in FIG. 7). Next, the next time window Tw2 is set in an overlapped time TI (see Step [6] in FIG. 7) and a slope of a frequency in this time window Tw2 is similarly obtained by least-square method and the slope is plotted. This calculation (moving calculation) is repeated sequentially to output a time-series change of the slope of the frequency of the air-pack pulse wave as a frequency slope time-series waveform (see Step [8] in FIG. 7)

Incidentally, the frequency computing means 631 can perform processing according to steps in FIG. 8 (hereinafter, called "zero-crossing method") instead of the processing according to steps in FIG. 7 (hereinafter, called "peak detecting method"). In the peak detecting method shown in FIG. 7, the frequency computing means 631 smoothing-differentiates the time-series waveform of the air-pack pulse wave obtained from the biological signal measuring device 1 to obtain a maximum value (peak value), but in the zero-crossing method shown in FIG. 8, a point (hereinafter, called "zero-crossing point") switching from a positive value to a negative value is obtained in the time-series waveform of the air-pack pulse wave. Then, the zero-crossing point is obtained for each 5 seconds, a reciprocal of a time interval between the zero-crossing points in the time-series waveform contained in the 5 seconds is obtained as an individual frequency f, and an average value of the individual frequency f in the 5 seconds is adopted as a value of a frequency F in the 5 seconds (see Step [1] in FIG. 8). Then, a time-series waveform of the frequency is obtained by plotting the frequency F obtained for each 5 seconds (see Step [2] in FIG. 8).

Figure 8:
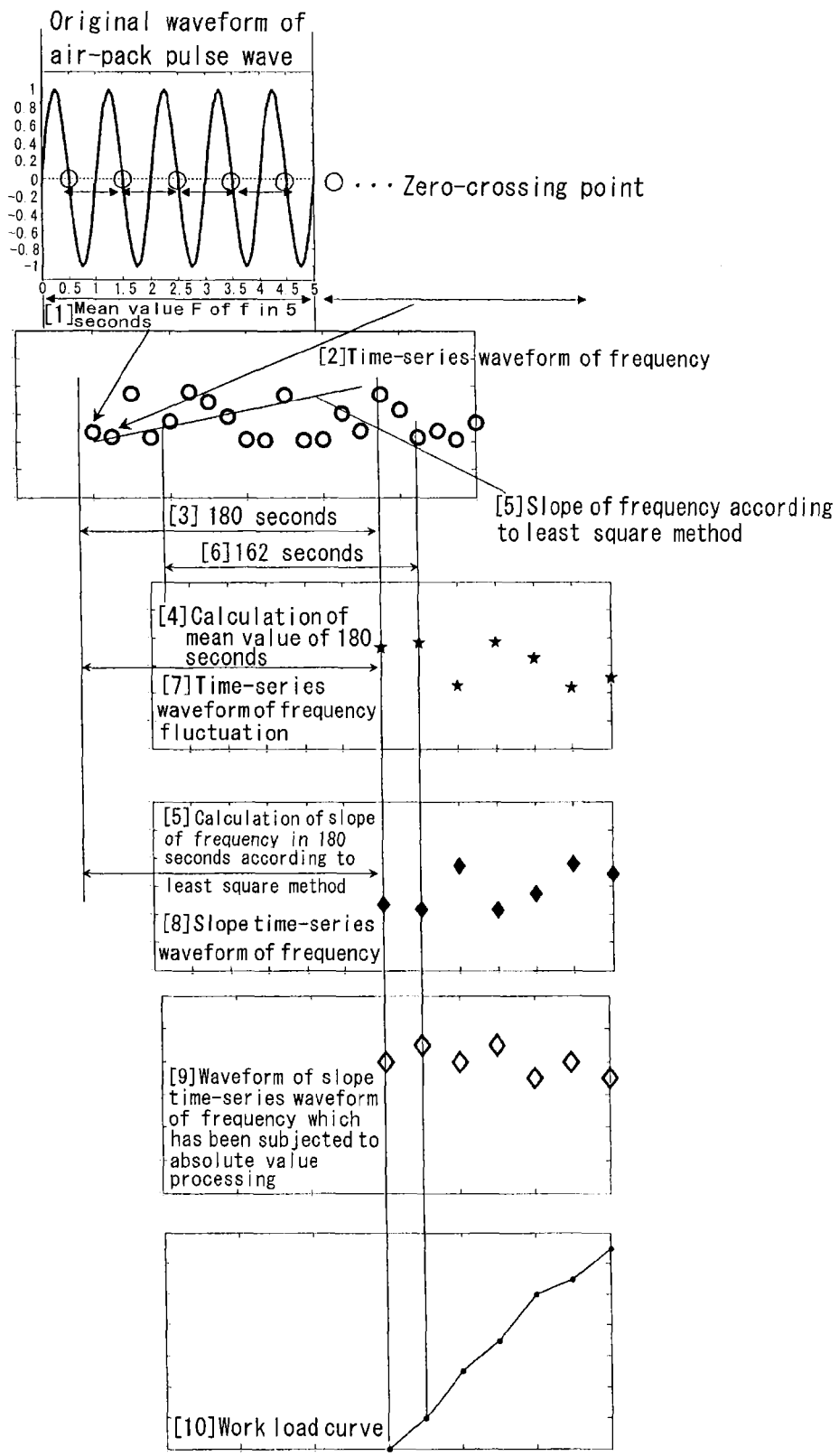
FIG. 8 is a diagram for describing a method for obtaining a frequency fluctuation time-series waveform, a base line of the frequency fluctuation time-series waveform, a frequency slope time-series waveform which is a slope time series of a frequency fluctuation, and an integral curve using a zero-crossing point of a biological signal (heartbeat fluctuation) detected by the biological signal measuring device.

Thereafter, like the case shown in FIG. 7, moving calculation is performed by the frequency fluctuation time-series analyzing and computing means 632 to obtain a frequency fluctuation time-series waveform (see Steps [3], [4], [6], and [7] in FIG. 8). Further, moving calculation is performed by the frequency slope time-series analyzing and computing means 633 to obtain a frequency slope time-series waveform (see Steps [3], [5], [6], and [8] in FIG. 8).

When the frequency slope time-series waveform, the frequency fluctuation time-series waveform and a base line thereof are used to determine a state of a person in the alcohol-drinking state determining means 650 described later, either one of the peak detecting method and the zero-crossing method can be used. It is preferred that, since which of the two methods shows clearer indication of a state of a person depends on differences among individuals, a more appropriate one of the two methods can be preliminarily set depending on individuals.

The alcohol-drinking state determining means 650 is composed of at least one of a plurality of programs, such as described below, which determine whether or not a person is in an alcohol-drinking state based upon the time-series fluctuation regarding the frequency obtained by the above-described various frequency dynamic information processing means 610 in this embodiment.

(a) Means for determining an alcohol-drinking state according to whether or not a dominant frequency time-series waveform obtained by the dominant frequency time-series waveform computing means 621 is higher than that obtained at a non-drinking time;

(b) Means for which determining an alcohol-drinking state according to whether or not a degree of fluctuation of the value of the dominant frequency of the dominant frequency time-series waveform in a predetermined time range is expanded more largely than that obtained at a non-drinking time;

(c) Means for determining an alcohol-drinking state according to whether or not a base line position of the dominant frequency fluctuation time-series waveform obtained by the dominant frequency fluctuation time-series analyzing and computing means 622 is higher than that obtained at a non-drinking time;

(d) Means for determining an alcohol-drinking state according to whether or not separation of a base line position of the dominant frequency fluctuation time-series waveform obtained by the dominant frequency fluctuation time-series analyzing and computing means 622 from the base line position of the dominant frequency slope time-series waveform obtained by the dominant frequency slope time-series analyzing and computing means 623 is larger than that obtained at a non-drinking time;

(e) Means for determining an alcohol-drinking state according to whether or not the base line position of the frequency fluctuation time-series waveform obtained by the frequency fluctuation time-series waveform analyzing and computing means 632 is higher than that obtained at a non-drinking time; and (f) Means for determining an alcohol-drinking state according to whether or not an integral value of a positive slope decreases by a preset difference or more and an integral value of a negative slope increases by a preset difference or more according to a process of separating the frequency slope time-series waveform obtained by the frequency slope time-series analyzing and computing means 633 into the positive slope and the negative slope to integrate the respective slopes and comparing the integral values with integral values obtained at a non-drinking time.

Since the alcohol-drinking state determining means 650 is provided with a plurality of determining means of the means (a) to (f), if setting is performed such that, when an alcohol-drinking state is determined in any one of these means, the fact (indicating an alcohol-drinking state) is outputted, a detection sensitivity of alcohol drinking can be elevated. On the other hand, setting can be performed such that, when an alcohol-drinking state is determined in, for example, at least two means among the means (a) to (f), the fact (indicating an alcohol-drinking state) is outputted. When the latter is adopted, such a merit can be obtained that detection error can be reduced. This makes it possible to perform setting with a proper combination of these means, for example, according to a purpose of diagnosis, a purpose of drunken driving detection or the like, depending on applications of the alcohol-drinking detecting system of this embodiment. Further, in respective cases, measurement results at a non-drinking time (the dominant frequency time-series waveform, the dominant frequency fluctuation time-series waveform, the dominant frequency slope time-series waveform, the frequency fluctuation time-series waveform, the frequency slope time-series waveform, and the integral value of the positive slope and the integral value of the negative slope obtained from the frequency slope time-series waveform) are preliminarily stored for each individual. When a measurement result is obtained at a certain time, the alcohol-drinking state determining means 650 reads the measurement result at a non-drinking time stored to compare the same with the measurement result at the certain time. Thereby, when a tendency separated from the case at a non-drinking time in each of the determining means (a) to (f) is indicated, the "alcohol-drinking state" can be determined. However, regarding a degree of separation to be determined as the "alcohol-drinking state", it is preferred that a threshold value is preliminarily set for each individual corresponding to each of the determining means (a) to (f) (namely, data about a degree of separation to be determined as an alcohol-drinking state obtained by comparing data at a non-drinking time and data at an alcohol-drinking time with each other is preliminarily taken to define a threshold value).

Incidentally, in the above-described embodiment, the air packs 10, and the first and second elastic members made of expanded resin beads 20 and 30 configuring the biological signal measuring device 1 are assembled into the automobile seat, but they may be assembled into not only the automobile seat but also into such bedding as a bed, a chair for diagnosis in a hospital facility or the like.

Test Example 1

Four Japanese healthy men (subjects A to D) in their 20s to 30s were made to sit on the above-described seat 500 as subjects and experiments were conducted. Incidentally, in the following, the air-pack pulse wave is an aortic pulse wave obtained from the biological signal measuring device 1 (hereinafter, called "air-pack sensor" in some cases) in a sitting state of each subject on the above-described seat 500. Further, the finger photoplethysmogram is obtained by measurement performed by an optical finger photoplethysmogram sphygmograph (Finger Clip Probe "SR-5C" manufactured by AMCO INC.) and the breath-alcohol concentration is obtained by measurement performed by "ALC-mini" (manufactured by TOKAI DENSHI INC.). Ethanol patch tests were preliminarily performed to the subjects on days different from the days on which the alcohol-drinking experiments to them were conducted, so that it was confirmed that they were of active type (NN type). Incidentally, regarding the weights and heights of the subjects, the subject A is a subject having a weight of 71 kg and a height of 167 cm, the subject B is a subject having a weight of 68 kg and a height of 178 cm, the subject C is a subject having a weight of 65 kg and a height of 171 cm, and the subject D is a subject having a weight of 59 kg and a height of 166 cm.

Figure 9:
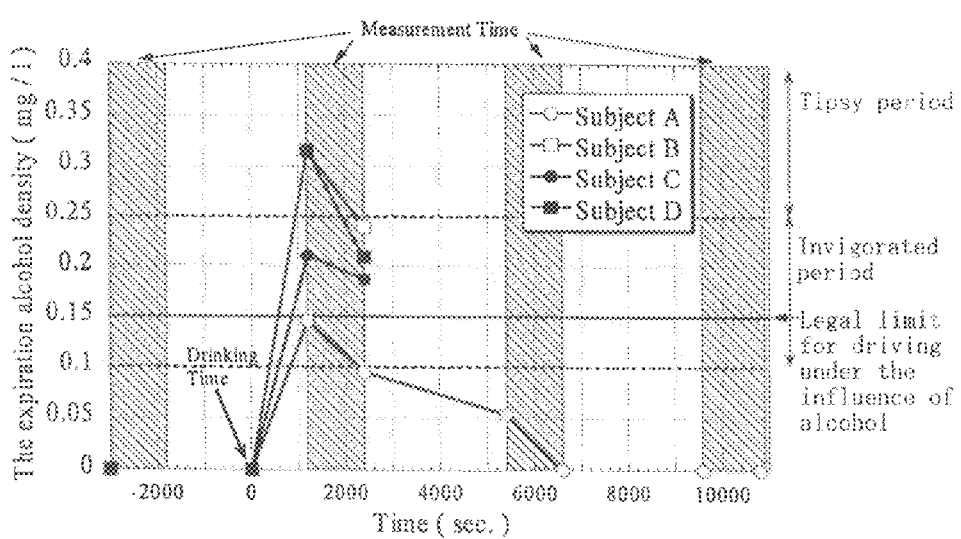
FIG. 9 is a diagram showing aspects of fluctuations of breath-alcohol concentrations (expiration alcohol density) of respective subjects measured by breath-alcohol concentrations.

Measurements of a biological signal performed by the air-pack sensor which was a non-invasive sensor and other sensors (an optical finger photoplethysmogram sphygmograph, a breath-alcohol concentration meter) were performed once in a period of 20 minutes before alcohol drinking, and the first measurements thereof were then performed in a period of 20 minutes after a period from 20 to 40 minutes elapsed after alcohol drinking (beer of 500 ml), it being considered that an alcohol concentration contained in blood of a person reaches the highest after alcohol drinking. Thereafter, regarding the subject A, measurements were performed a total of four times; two times at a fixed interval in a period from 90 to 110 minutes and two times at a fixed interval in a period from 160 to 180 minutes in order to see change according to time elapsing. Each subject was put in a state where he did not have a meal for at least three hours before an alcohol-drinking start time, where a state close to hunger was reconstructed. Further, the subject ate an appropriate amount of snacks during alcohol drinking in order to simulate an ordinary alcohol-drinking state. Further, the subject received only water in addition to the snacks without conducting further alcohol drinking and eating during experiment. The breath-alcohol concentration was measured before and after measurement of the biological signal. An aspect of fluctuation of the breath-alcohol concentration is shown in FIG. 9.

Figure 10A:
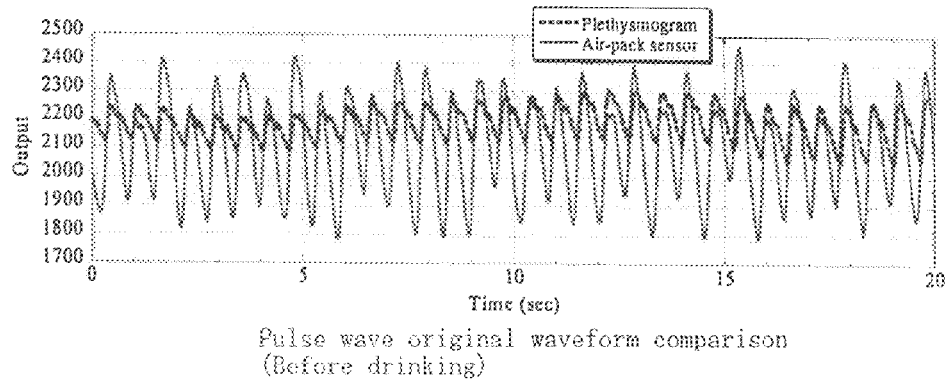
FIG. 10A is a diagram showing original waveforms of a finger photoplethysmogram biological signal and an air-pack pulse wave for a period of 5 minutes from a start of measuring in a non-drinking state of a subject A.
Figure 10B:
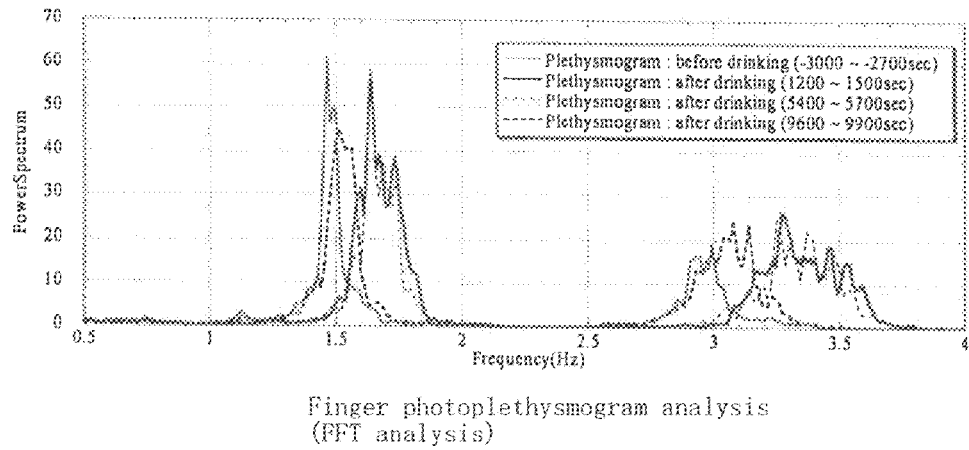
FIG. 10B is a diagram showing a frequency-analysis result of the finger photoplethysmogram.
Figure 10C:
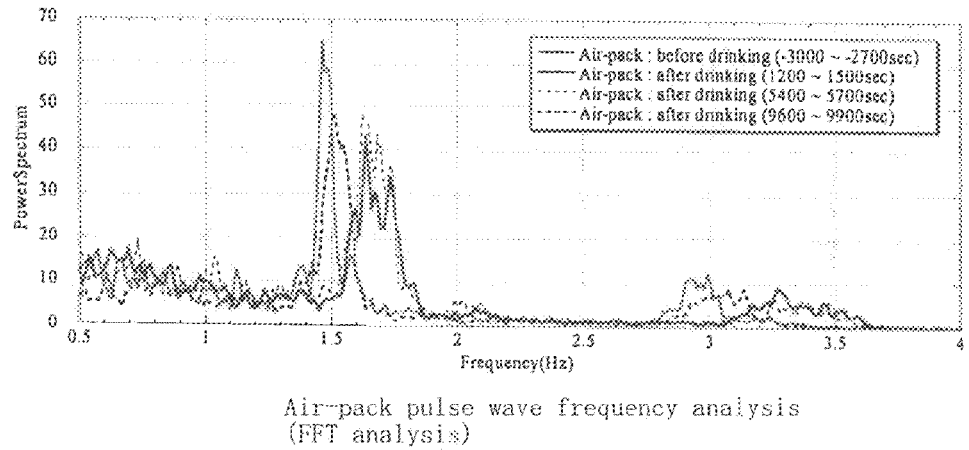
FIG. 10C is a diagram showing a frequency-analysis result of the air-pack pulse wave.

FIGS. 10A to 10C show original waveforms of data of a finger photoplethysmogram and an air-pack pulse wave (aortic pulse wave) of the subject A for 5 minutes from the start of measurement, respectively, and frequency analyzing results for the 5 minutes. Peak positions of the dominant frequencies of the finger photoplethysmogram and the air-pack pulse wave approximately coincide with each other, from which it is understood that biological signals having equivalent frequency characteristic are obtained in the finger photoplethysmogram and the air-pack pulse wave.

FIG. 11 shows a transition of a dominant frequency of an air-pack pulse wave of the subject A obtained by the dominant frequency time-series waveform computing means 621 without overlapping respective time windows of 300 seconds with one another. FIG. 11 also shows a transition of the dominant frequency of a finger photoplethysmogram for each 300 seconds. Fluctuation of the frequency of the air-pack pulse wave corresponding to rising of the breath-alcohol concentration due to alcohol drinking is confirmed from FIG. 9 to FIG. 11 and a state where the heart rate has risen due to the alcohol drinking can be detected. It is also understood that lowering of the breath-alcohol concentration occurs to come close to the heart rate before alcohol drinking with time elapsing. Further, it is understood from FIG. 11 that the degree of fluctuation of the dominant frequency is further expanded in a period from 20 to 40 minutes after alcohol drinking and in a period from 90 to 110 minutes thereafter as compared with that before alcohol drinking. The degree of fluctuation of the dominant frequency is slightly expanded even in a period from 160 to 180 minutes after alcohol drinking. Accordingly, it can be understood that the alcohol-drinking state can be determined by determining whether or not the degree of fluctuation of the value of the dominant frequency is expanded. Incidentally, this point is similarly applied to the cases shown in FIG. 12 and FIG. 13.

FIG. 12 shows details of a transition of the dominant frequency obtained for each time window, the time window being set to 90 seconds in a 90%-overlapping time, by the dominant frequency time-series waveform computing means 621. FIG. 13 shows details of a transition of the dominant frequency obtained for each time window, the time window being set to 300 seconds in a 90%-overlapping time, by the dominant frequency time-series waveform computing means 621.

From FIG. 9, the breath-alcohol concentration of about 0.15 mg/l which was a boundary value of a legal limit for driving under the influence of alcohol was detected in a period from 20 to 40 minutes after alcohol drinking from the subject A and the breath-alcohol concentration of 0.05 mg/l or less was also detected in a period from 90 to 110 minutes after alcohol drinking.

In FIG. 12, while the dominant frequency time-series waveform before alcohol drinking transitions in a range of approximately 1.4 to 1.55 Hz and the dominant frequency time-series waveform in a period from 160 to 180 minutes after alcohol drinking transitions in a range of approximately 1.45 to 1.55 Hz, the dominant frequency time-series waveform transitions in a range of approximately 1.52 to 1.75 Hz in a period from 20 to 40 minutes after alcohol drinking and it transitions in a range of approximately 1.49 to 1.75 Hz in a period from 90 to 110 minutes after alcohol drinking, where the dominant frequency time-series waveform lies in high tendency in whole. Accordingly, it is understood that the alcohol-drinking state determining means 650 can determine the alcohol-drinking state by comparing the dominant frequency time-series waveform with that before alcohol drinking.

Further, the degree of fluctuation of the dominant frequency is 0.15 Hz before alcohol drinking, but it is expanded to 0.23 Hz in a period from 20 to 40 minutes after alcohol drinking and it is also expanded to 0.26 Hz in a period from 90 to 110 minutes after alcohol drinking. The degree of fluctuation is reduced again to 0.1 Hz in a period from 160 to 180 minutes after alcohol drinking. Accordingly, it is understood that the alcohol-drinking state can be determined by setting the threshold of the degree of fluctuation.

In the case shown in FIG. 13, the dominant frequency time-series waveform before alcohol drinking transitions in a range of approximately 1.44 to 1.46 Hz (it is supposed that a projected value at a time point of 800-seconds elapsing occurs due to body motion) (the degree of fluctuation is 0.02 Hz), but the dominant frequency time-series waveform in a period from 20 to 40 minutes after alcohol drinking is in a range of approximately 1.55 to 1.64 Hz (the degree of fluctuation is 0.09 Hz), the dominant frequency time-series waveform in a period from 90 to 110 minutes after alcohol drinking is in a range of approximately 1.55 to 1.62 Hz (the degree of fluctuation is 0.07 Hz), and the dominant frequency time-series waveform in a period from 160 to 180 minutes after alcohol drinking is in a range of approximately 1.44 to 1.52 Hz (the degree of fluctuation is 0.08 Hz), from which it is understood that the dominant frequency time-series waveform tends to be high in whole and the degree of fluctuation tends to expand due to alcohol drinking.

Figure 14A:
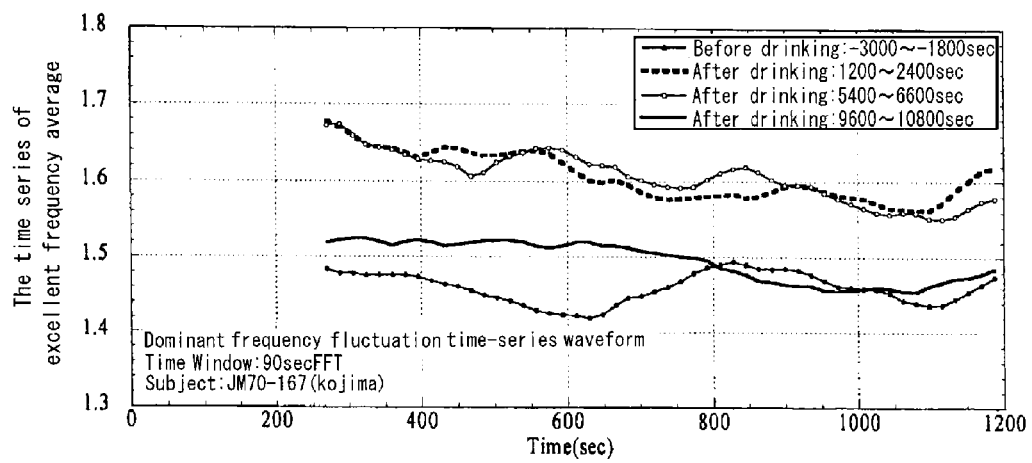
FIG. 14A is a diagram showing dominant frequency fluctuation time-series waveforms obtained from the dominant frequency time-series waveforms shown in FIG. 12.
Figure 14B:
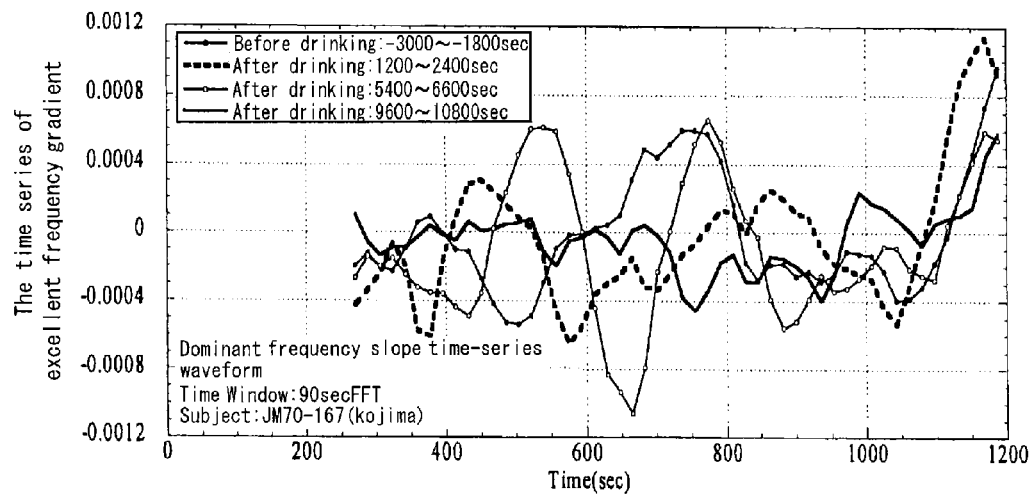
FIG. 14B is a diagram showing dominant frequency slope time-series waveforms obtained from the dominant frequency time-series waveforms shown in FIG. 12.
Figure 15A:
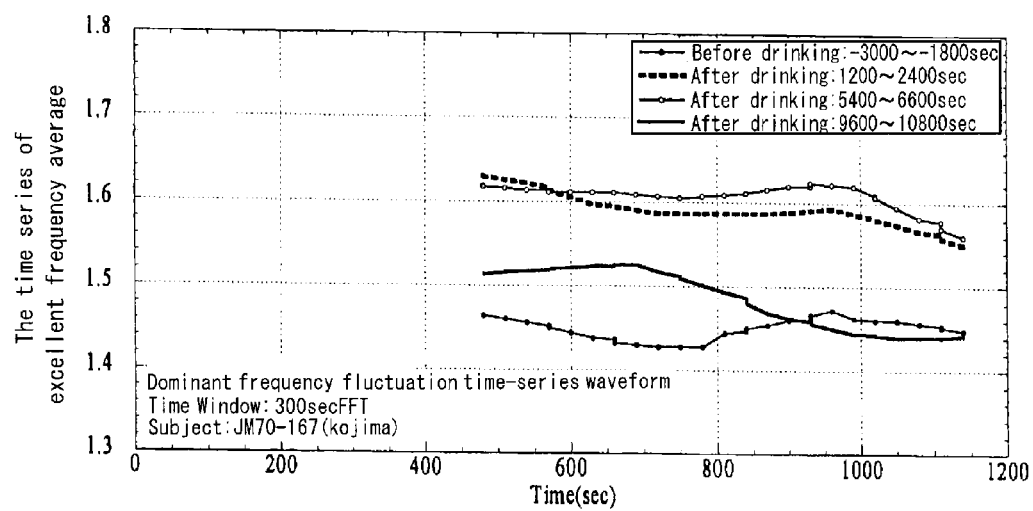
FIG. 15A is a diagram showing dominant frequency fluctuation time-series waveforms obtained from the dominant frequency time-series waveforms shown in FIG. 13.
Figure 15B:
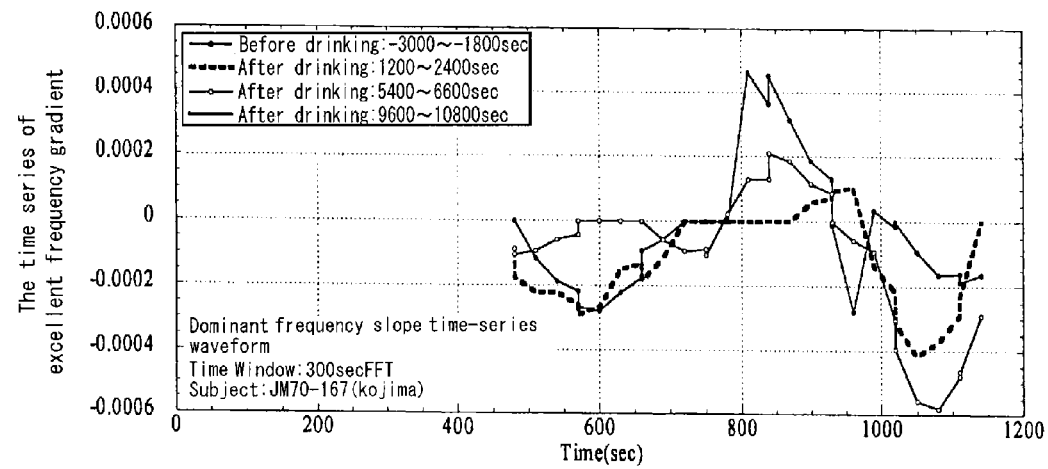
FIG. 15B is a diagram showing dominant frequency slope time-series waveforms obtained from the dominant frequency time-series waveforms shown in FIG. 13.

FIGS. 14A and 14B and FIGS. 15A and 15B are output graphs of dominant frequency fluctuation time-series waveforms obtained by the dominant frequency fluctuation time-series analyzing and computing means 622 and dominant frequency slope time-series waveforms obtained by the dominant frequency slope time-series analyzing and computing means 623, FIGS. 14A and 14B being graphs obtained by setting the time window to 90 seconds and FIGS. 15A and 15B being graphs obtained by setting the time window to 300 seconds. As apparent from these graphs, it is understood that the base line positions of the dominant frequency fluctuation time-series waveforms are approximately 1.6 Hz or so both in a period from 20 to 40 minutes after alcohol drinking and in a period from 90 to 110 minutes after alcohol drinking, and the base line positions of the dominant frequency fluctuation time-series waveforms are approximately 1.5 Hz or so before alcohol drinking and in a period from 160 to 180 minutes after alcohol drinking, so that, when the former positions and the latter positions are compared with each other, the former positions obviously become higher than the latter positions. Therefore, for example, the threshold is set to 1.6 Hz and when the base line position reaches 1.6 Hz or higher, the alcohol-drinking state determining means 650 can determine the alcohol-drinking state. Incidentally, it is preferred that a value of the threshold to be set can be set for each individual.

Figure 16A:
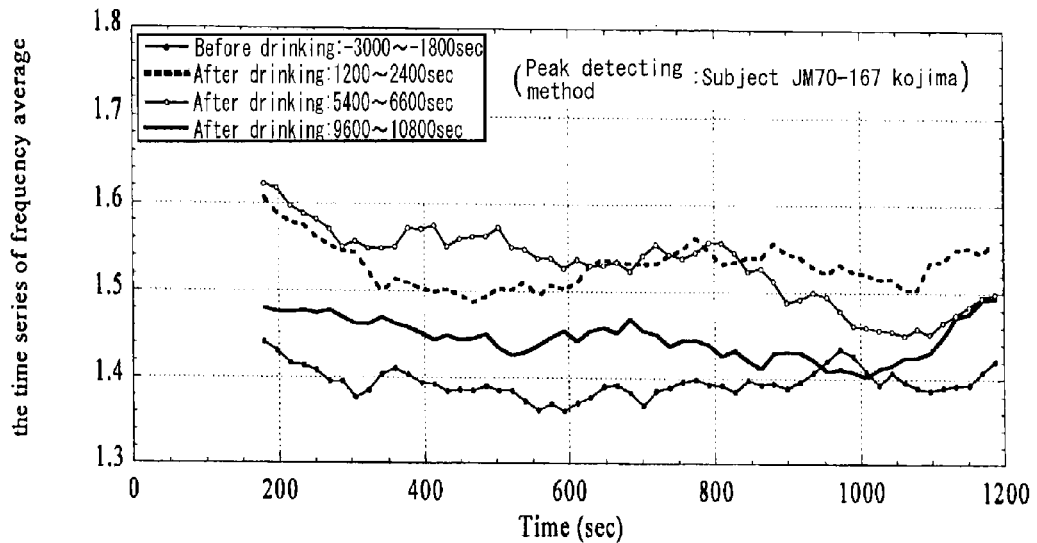
FIG. 16A is a diagram showing frequency fluctuation time-series waveforms of air-pack pulse waves of the subject A obtained by a frequency fluctuation time-series analyzing and computing means and FIG. 16B is a diagram showing frequency slope time-series waveforms of air-pack pulse waves of the subject A obtained by a frequency slope time-series analyzing and computing means.
Figure 16B:
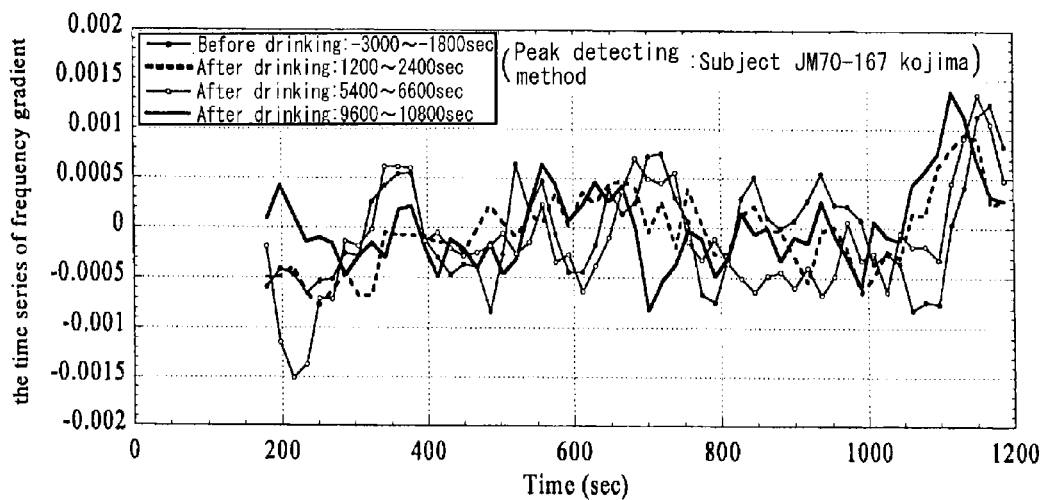
Figure 17A:
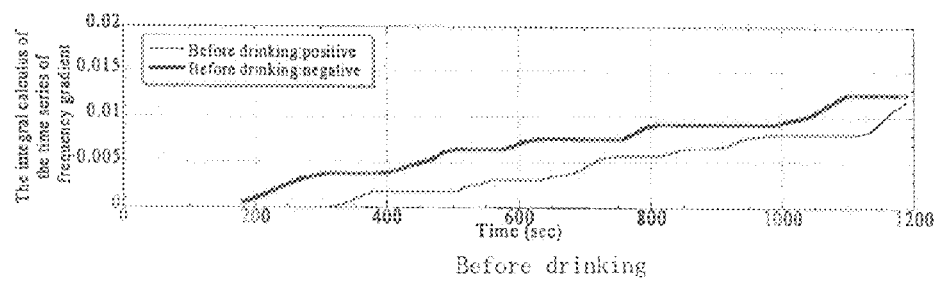
FIGS. 17A to 17D are diagrams showing waveforms obtained by integrating a positive slope and a negative slope of a frequency slope time-series waveform of the subject A in a dividing manner.
Figure 17B:
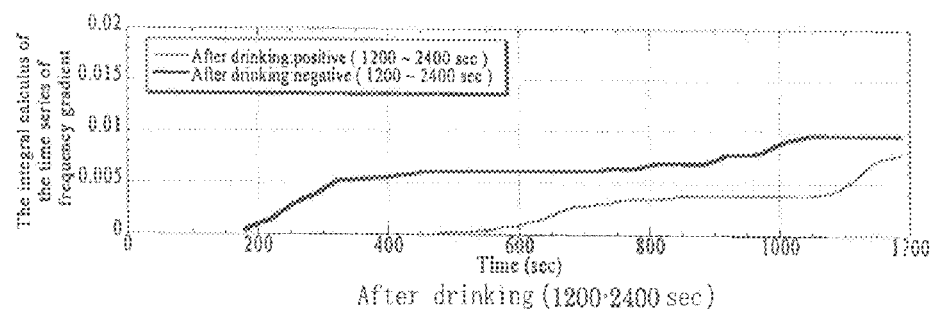
Figure 17C:
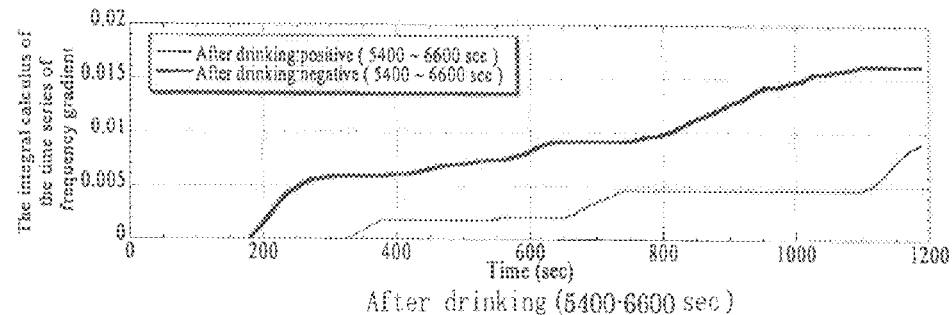
Figure 17D:
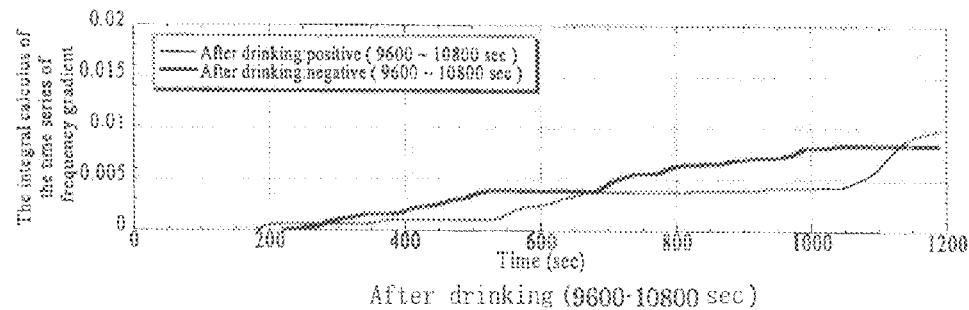

FIGS. 16A and 16B show frequency fluctuation time-series waveforms and frequency slope time-series waveforms of an air-pack pulse wave of the subject A obtained by the frequency fluctuation time-series analyzing and computing means 632 and the frequency slope time-series analyzing and computing means 633.

The base line position of the frequency fluctuation time-series waveform obtained by the frequency fluctuation time-series analyzing and computing means 632 is about 1.37 to 1.44 Hz before alcohol drinking but it is in a range of 1.5 to 1.55 Hz in a period from 20 to 40 minutes after alcohol drinking, it is in a range of 1.5 Hz to 1.6 Hz in a period from 90 to 110 minutes after alcohol drinking, and it is in a range of about 1.4 to 1.5 Hz in a period from 160 to 180 minutes after alcohol drinking, from which it is understood that the base line position at an alcohol-drinking time becomes higher than that at a non-drinking time. Accordingly, by setting the threshold value of the base line position, the alcohol-drinking state can be determined by the alcohol-drinking state determining means 650.

Further, when the frequency fluctuation time-series waveforms shown in FIGS. 16A and 16B are observed, the value of the frequency before alcohol drinking transitions approximately horizontally over a whole region of a test time period while fluctuating slightly vertically, but it transitions with a lowering tendency of downward to the right in a period from the start of the test to about 1000 seconds in a period from 20 to 40 minutes after alcohol drinking, in a period from 90 to 110 minutes after alcohol drinking, and in a period from 160 to 180 minutes after alcohol drinking, and it lies in a rising tendency up to test termination after elapsing of 1000 seconds. This test is a test where the subject sits on the seat 500 for 20 minutes, but the subject fatigues with time elapsing. At this time, if the subject is in a state before alcohol drinking, since a compensating action of a sympathetic nerve functions against progress of fatigue to accommodate the progress by raising an activation level, the frequency fluctuation time-series waveform does not show the lowering tendency of downward to the right. However, when a biological body falls in a resting mode due to alcohol drinking, since the compensating action of the sympathetic nerve does not function, heartbeat fluctuation tends to lower. Thereby, it is thought that the frequency fluctuation time-series waveform transitions with a lowering tendency of downward to the right. Therefore, when the alcohol-drinking state is determined according to not only the base line position of the frequency fluctuation time-series waveform but also whether or not the frequency fluctuation time-series waveform transitions with a lowering tendency of downward to the right, the determination accuracy is improved. Incidentally, the reason why the frequency fluctuation time-series waveform rises just before termination of the test is because such a stimulation that the test will terminate soon is inputted.

FIGS. 17A to 17D show integral values (integral calculus) of the frequency slope time-series waveforms shown in FIG. 16B. Specifically, a positive slope and a negative slope of the frequency slope time-series waveforms shown in FIG. 16B were integrated independently from each other. When the integral values of the slope time-series waveforms of the frequency fluctuation before and after alcohol drinking are compared with each other, it is understood that the negative component tends to increase according to increase of the breath-alcohol concentration, but when the lowering of the breath-alcohol concentration occurs, the negative component returns to a state similar to the state before alcohol drinking. Further, the positive component decreases according to increase of the breath-alcohol concentration, while it increases when decrease of the breath-alcohol concentration occurs. This is because the slope time-series waveform of the frequency fluctuation expresses the degree of fluctuation of the frequency component of the air-pack pulse wave, from which, it is understood that an aspect of the fluctuation of the frequency fluctuation of the air-pack pulse wave changes due to alcohol drinking. Accordingly, the alcohol-drinking state determining means 650 can perform comparison with the integral value in a normal state before alcohol drinking to determine the alcohol-drinking state according to whether or not the integral value of the positive slope decreases to a difference preset or more and the integral value of the negative slope increases to a difference preset or more.

Figure 18:
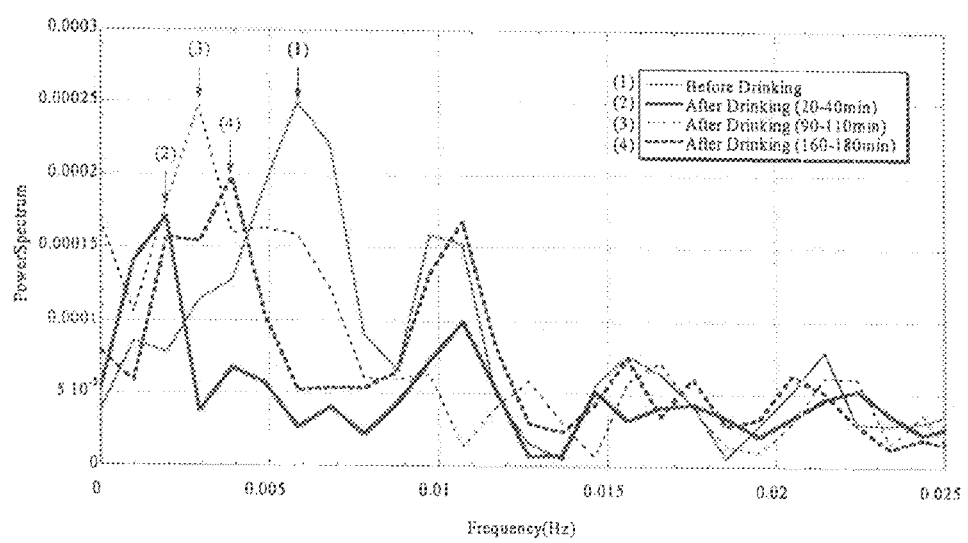
FIG. 18 is a diagram showing a frequency-analysis result of the frequency slope time-series waveforms shown in FIG. 16.

FIG. 18 shows the frequency analysis result of the slope time-series waveforms of the frequency fluctuations shown in FIG. 16B. It is understood that the dominant frequency peak transitions to a low frequency side according to increase of the breath-alcohol concentration due to alcohol drinking. Thereafter, the dominant frequency peak transitions to a high frequency side according to lowering of the breath-alcohol concentration. This suggests that the transition coincides with the aspect of fluctuations of the integral values shown in FIGS. 17A to 17D, and a chaotic property disappears from fluctuation of the frequency fluctuation of the air-pack pulse wave due to alcohol drinking so that the fluctuation becomes monotonous.

Figure 19A:
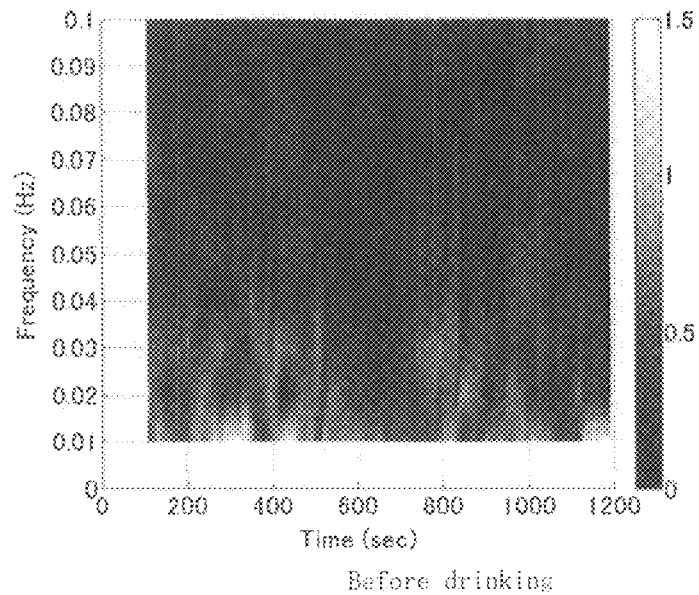
FIGS. 19A and 19B are diagrams showing a power spectrum of an air-pack pulse wave where change of the overlapping time to 90 seconds in the time window of 100 seconds was performed using Lyapunov exponent of an air-pack pulse wave.
Figure 19B:
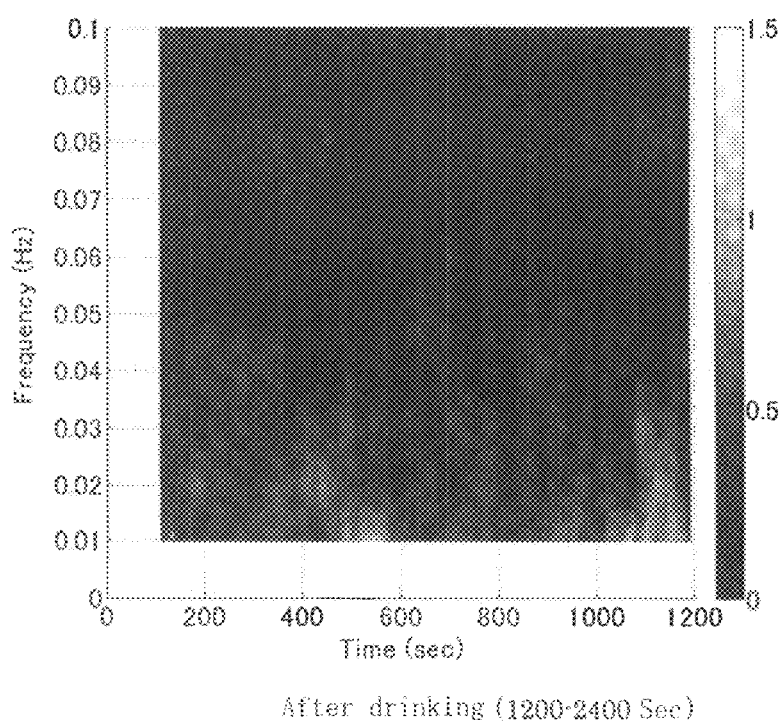
Figure 20A:
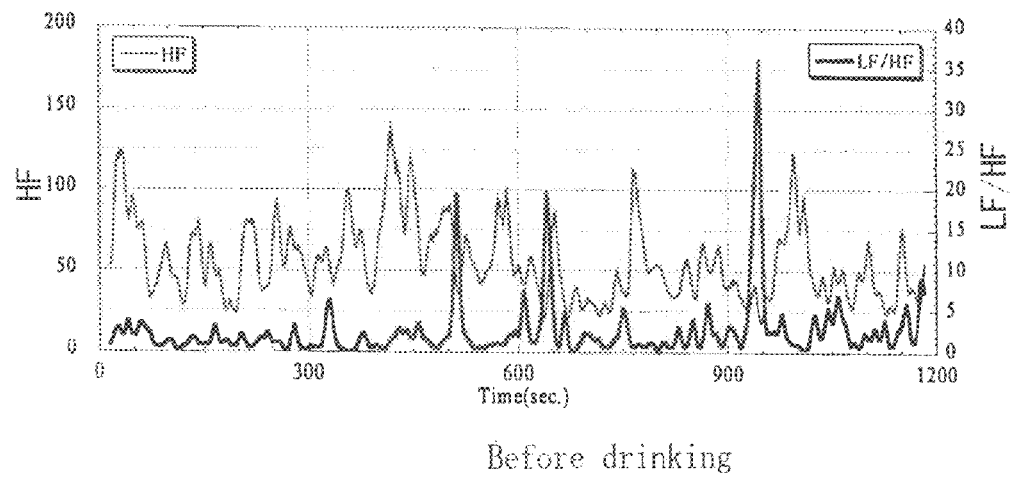
FIGS. 20A to 20D are diagrams showing wavelet-analysis results of pulse rate fluctuations obtained from finger photoplethysmograms of the subject A.
Figure 20B:
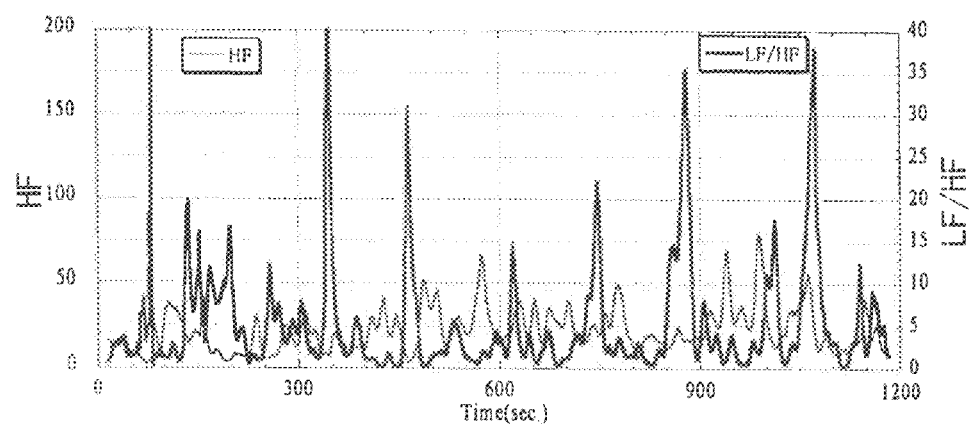
Figure 20C:
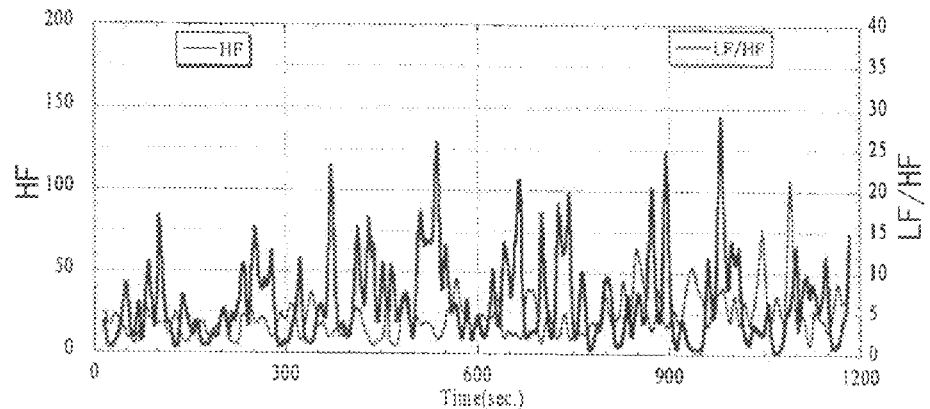
Figure 20D:
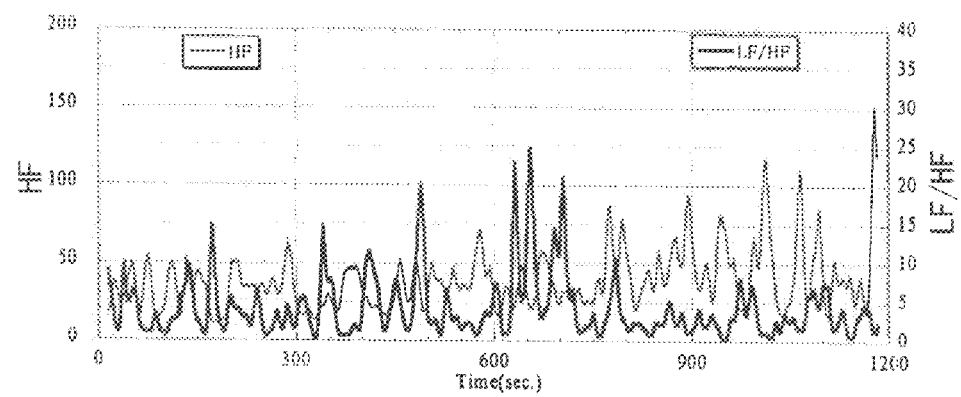

FIGS. 19A and 19B show power spectrums of the air-pack pulse wave where the overlapping time was changed to 90 seconds in the time window of 100 seconds using Lyapunov exponent of the air-pack pulse wave. A level of the fluctuation of Lyapunov exponent of the air-pack pulse wave due to alcohol drinking is expressed by a level of the power spectrum. It is also understood from the lowering of the power spectrum that increase of the breath-alcohol concentration due to alcohol drinking reduces the fluctuation of the frequency fluctuation of the air-pack pulse wave.

FIGS. 20A to 20D show a wavelet analysis result of pulse rate fluctuation obtained from the finger photoplethysmogram of the subject A. A ratio of occurrence of a burst wave of LF/HF representing influence of a sympathetic nerve increases and a level of a base line of HF lowers due to alcohol drinking. It is thought that the analysis result shows sympathetic hyperactivity due to alcohol drinking. It is estimated that parasympathetic nerve (vagus nerve) activity of a heart after alcohol drinking is suppressed as compared with that at rest before alcohol drinking and sympathetic nerve activity is in a hyperactivity state. Further, it is indicated from a chaos analysis of the pulse wave that the pulse wave becomes simple and the chaotic property lowers in such a case that a pulse wave is mechanically produced by IABP (intra-aortic balloon pumping) during the IABP due to sympathetic nerve tone state or cardiac infraction. It is thought from these findings that reduction of the fluctuation of the frequency of the finger photoplethysmogram/air-pack pulse wave caused by increase of the breath-alcohol concentration due to alcohol drinking is associated with the sympathetic hyperactivity due to alcohol drinking and simplification of the pulse wave caused thereby. Further, it was confirmed that the sympathetic hyperactivity was suppressed according to decrease of the breath-alcohol concentration due to time elapsing, but it was also confirmed that the alcohol-drinking state was different from a state before alcohol drinking and it involved tension so that it did not return to a relaxing state completely. Incidentally, a result similar to the result in this text example was obtained in test cases in the remaining three subjects.

Figure 21:
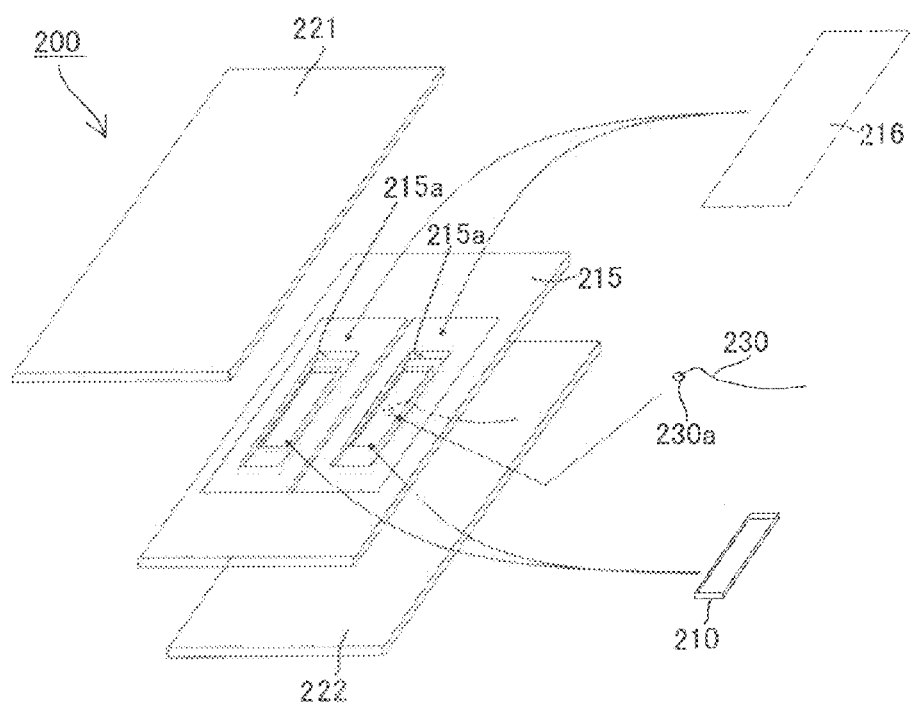
FIG. 21 is a view showing one example of a biological signal measuring device according to another embodiment.

Further, the biological signal measuring device is not limited to ones using the above-described air pack 10, but a device shown in FIG. 21 can be used. A biological signal measuring device 200 shown in FIG. 21 is configured to have a three-dimensional solid knitted fabric 210, a three-dimensional solid knitted fabric supporting member 215, a film 216, plate-shaped expanded bodies 221, 222, and a vibration sensor 230.

As the three-dimensional solid knitted fabric 210, one similar to the material used in the biological signal measuring device 1 shown in FIG. 1 and the like can be used. It is preferred that the three-dimensional solid knitted fabric 210 has a load-deflection characteristic in a thickness direction where when it is placed on a measurement plate and it is pressed by a pressing plate having a diameter of 30 mm or a diameter of 98 mm, a spring constant falls in a range up to a load of 100N and is similar to a load-deflection characteristic of a muscle of the breech of a person. Specifically, it is preferred that a three-dimensional solid knitted fabric having a spring constant which falls in a range of 0.1 to 5 N/mm when it is pressed by the pressing plate having a diameter of 30 mm or having a spring constant which falls in a range of 1 to 10 N/mm when it is pressed by the pressing plate having a diameter of 98 mm. Since the load-deflection characteristic of the three-dimensional solid knitted fabric 210 is similar to the load-deflection characteristic of the muscle of the breech of a person, the three-dimensional solid knitted fabric and the muscle are balanced, so that when a biological signal is transmitted to the three-dimensional solid knitted fabric, the three-dimensional solid knitted fabric vibrates similarly to the muscle of a person, whereby transmission of the biological signal can be performed without causing large damping.

It is preferred that the plate-shaped expanded bodies 221, 222 are composed of expanded bead bodies. As the expanded bead body, for example, an expanded formation body of a resin containing at least one of polystyrene, polypropylene, and polyethylene according to a bead method can be used. The plate-shaped expanded bodies 221, 222 composed of expanded bead bodies transmit a biological signal involving fine vibrations as a membrane oscillation (transverse wave) according to characteristics of spherical resin membranes formed of foams constituting individual fine beads. The membrane oscillation (transverse wave) is transmitted to the three-dimensional solid knitted fabric as a string vibration, and these membrane oscillation (transverse wave) and string vibration are overlapped with each other, so that the biological signal is detected by a vibration sensor 230 described later as a mechanical vibration amplified by overlapping of the membrane oscillation (transverse wave) and the string vibration with each other. Accordingly, detection of the biological signal is made easy.

When the plate-shaped expanded bodies 221, 222 are composed of expanded bead bodies, it is preferred that an expansion ratio is in a range of 25 to 50 times and a thickness of the bodies is set to be equal to or less than an average diameter of beads. For example, when an average diameter of beads having an expansion ratio of 30 times is in a range of about 4 to 6 mm, the plate-shaped expanded bodies 221, 222 are sliced cut to have a thickness of about 3 to 5 mm. Thereby, soft elasticity is imparted to the plate-shaped expanded bodies 221, 222, so that the plate-shaped expanded bodies 221, 222 resonate with small vibration with small amplitude, which results in difficulty in occurrence of damping in a transverse wave propagating on a film. Incidentally, the plate-shaped expanded bodies 221, 222 may be disposed on both sides of the three-dimensional solid knitted fabric 210 in a sandwiching manner like this embodiment, but such a configuration can be adopted that the plate-shaped expanded body is disposed only on one side of the three-dimensional solid knitted fabric 210, preferably, it is disposed only on the side of the seatback.

Here, as the three-dimensional solid knitted fabric 210, a reed-shaped one having a width of 40 to 100 mm and a length of 100 to 300 mm is used. When a three-dimensional solid knitted fabric 210 having such a size is used, pre-compression (a state where tension occurs in connection strands) occurs easily, and a balanced state between a person and the three-dimensional solid knitted fabric 210 is produced easily. In this embodiment, two three-dimensional solid knitted fabrics are disposed at positions symmetrical to each other so as to sandwich a site corresponding to a backbone in order to reduce a feeling of discomfort when the back of a person abuts on the seatback. It is preferred that such a configuration is adopted in order to dispose the three-dimensional solid knitted fabrics 210 at predetermined positions easily, the three-dimensional solid knitted fabrics 210 are supported by a three-dimensional solid knitted fabric supporting member 215, as shown in FIG. 21. The three-dimensional solid knitted fabric supporting member 215 is formed in a plate shape, and is also formed with two vertically-long through-holes for arrangement 215a, 215a at positions symmetrical to each other so as to sandwich a site corresponding to a backbone. It is preferred that the three-dimensional solid knitted fabric supporting member 215 is composed of a expanded bead body formed in a plate shape like the above-described plate-shaped expanded bodies 221, 222. Preferable expansion ratio and thickness range when the three-dimensional solid knitted fabric supporting member 215 is composed of an expanded bead body are similar to those of the above-described plate-shaped expanded bodies 221, 222. However, in order to cause a biological signal to generate membrane oscillation (transverse wave) more significantly, it is preferred that the thickness of the plate-shaped expanded bodies 221, 222 disposed above and below the three-dimensional solid knitted fabrics 210, 210 in a stacking manner is thinner than that of the three-dimensional solid knitted fabric supporting member 215.

In a state where two three-dimensional solid knitted fabrics 210, 210 are inserted and disposed in the through-holes for arrangement 215a, 215a formed in the three-dimensional solid knitted fabric supporting member 215, films 216, 216 are stacked on surface sides and back surface sides of the three-dimensional solid knitted fabrics 210, 210. It is preferred that formation positions of the through-holes for arrangement 215a, 215a (namely, arrangement positions of the three-dimensional solid knitted fabrics 210, 210) are set to positions corresponding to regions where fluctuation occurring due to motion involved in pumping of an atrium and an aorta (especially, a descending aorta) and motion (aortic pulse wave) of an aorta valve can be detected. As a result, the three-dimensional solid knitted fabrics 210, 210 are sandwiched in their upper and lower faces between the plate-like expanded bodies 221, 222, and peripheral portions thereof are surrounded by the three-dimensional solid knitted fabric supporting member 215, so that the plate-like expanded bodies 221, 222, and the three-dimensional solid knitted fabric supporting member 215 serve as resonant-vibration boxes (resonance boxes).

Further, it is preferred that the three-dimensional solid knitted fabrics 210, 210 thicker than the three-dimensional solid knitted fabric supporting member 215 are used. That is, such a thickness relationship that, when the three-dimensional solid knitted fabrics 210, 210 are disposed in the through-holes for arrangement 215a, 215a, surfaces and back surfaces of the three-dimensional solid knitted fabrics 210, 210 are protruded beyond the through-holes for arrangement 215a, 215a is satisfied. Thereby, when peripheries of the films 216, 216 are made to adhere to peripheral edge portions of the through-holes for arrangement 215a, 215a, the three-dimensional solid knitted fabrics 210, 210 are pressed in a thickness direction thereof, so that tensions are produced due to reaction forces of the films 216, 216, which results in easy occurrence of solid vibration (membrane oscillation (transverse wave)) in the films 216, 216. On the other hand, pre-compression also occurs in the three-dimensional solid knitted fabrics 210, 210 and tension due to reaction force also occurs in connecting strands holding a thickness shape of the three-dimensional solid knitted fabric, which results in easy occurrence of string vibration. Incidentally, it is preferred that the films 216, 216 are provided on both sides of the surface sides and the back surface sides of the three-dimensional solid knitted fabrics 210, 210, but such a configuration can be adopted that the films are provided on one sides of the three-dimensional solid knitted fabrics 210, 210. As the films 216, 216, plastic films made of polyurethane elastomer (for example, Product Number "DUS605-CDR" produced by Sheedom Co., Ltd.) or the like can be used.

The vibration sensor 230 is disposed in one three-dimensional solid knitted fabric 210 in a fixed state before stacking of the above-described films 216, 216. The three-dimensional solid knitted fabric 210 is composed of a pair of ground knitted fabrics and connecting strands, but since string vibrations of respective connecting strands are transmitted to the films 216, 216 and the plate-shaped expanded bodies 221, 222 through node points with the ground knitted fabric, it is preferred that a sensing portion 230a of the vibration sensor 230 is fixed to a surface of the three-dimensional solid knitted fabric 210 (a surface of the ground knitted fabric). It is preferred that as the vibration sensor 230, a microphone sensor, especially, a capacitive microphone sensor, is used. In this embodiment, since it is unnecessary to consider a sealing property of a site where the microphone sensor has been disposed (namely, the through-hole for arrangement 215a in which the three-dimensional solid knitted fabric 210 has been disposed), lead wires of the microphone sensor can be wired easily. A vibration of a body surface generated by a biological signal via a muscle of a person is transmitted to not only the three-dimensional solid knitted fabric 210 but also the plate-shaped expanded bodies 221, 222 and the film 216, so that it is amplified due to overlapping of vibrations (string vibration and membrane oscillation (transverse wave)) of these members whilst damping is prevented. Therefore, the vibration sensor 230 is not limited to fixation to the three-dimensional solid knitted fabric 210 but the sensing portion 230a thereof may be fixed to the plate-shaped expanded bodies 221, 222 and the film 216 configuring a vibration transmission route.

Figure 22A:
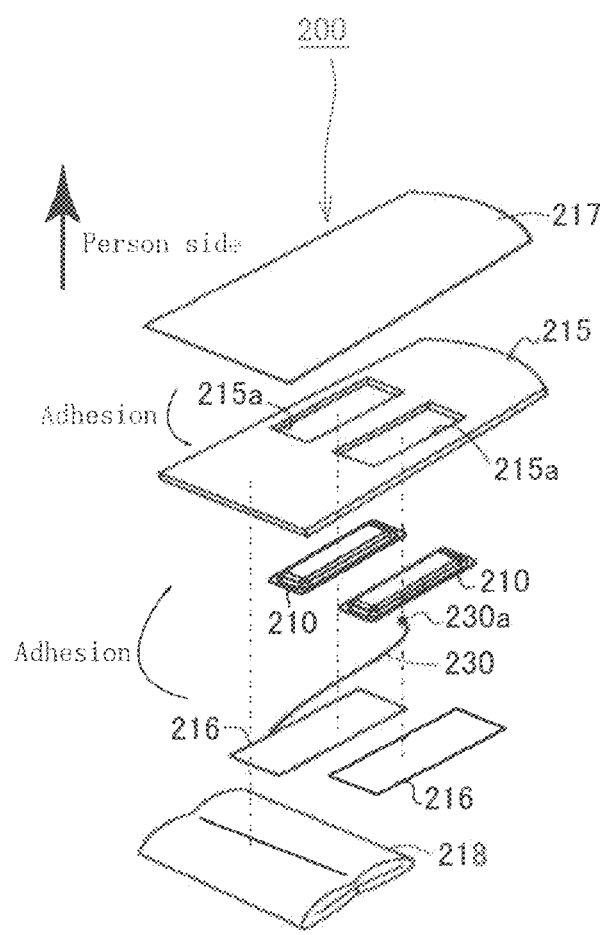
FIGS. 22A and 22B are views showing other examples of a biological signal measuring device according to another embodiment.
Figure 22B:
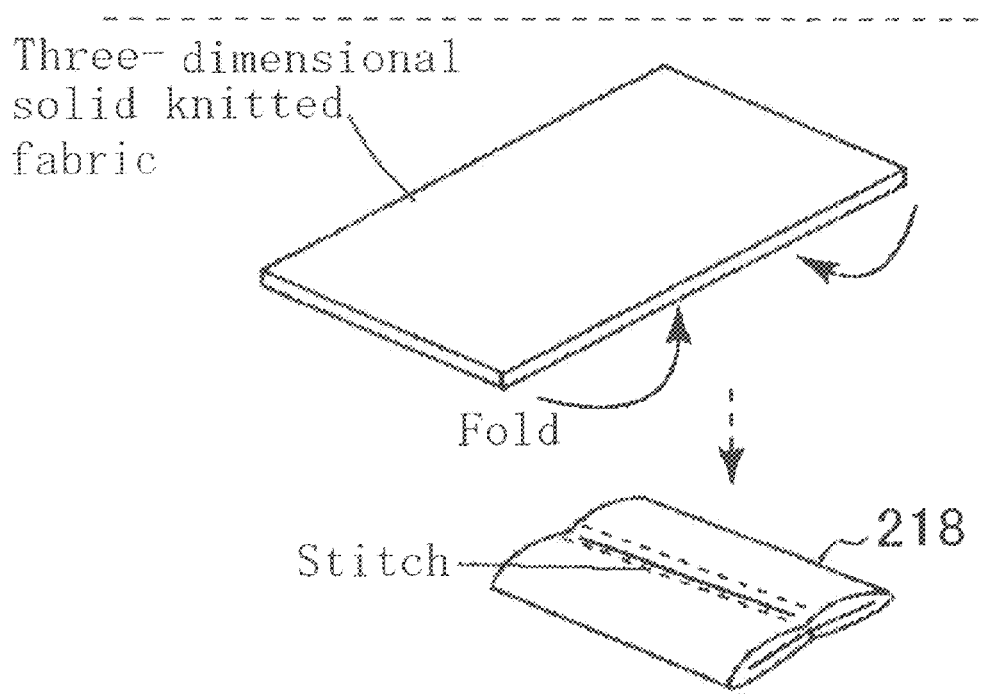

The biological signal measuring device 200 is not limited to the device shown in FIG. 21, but a film 217 having such a size that it can cover both of two three-dimensional solid knitted fabrics 210, 210 can be used in at least one of the knitted fabrics 210, 210, as shown in FIG. 22A. Further, as shown in FIG. 22B, a lumber support 218 obtained by folding an approximately rectangle-shaped three-dimensional solid knitted fabric from both side edges thereof toward a center thereof and stitching a central portion of an overlapped portion of the knitted fabric may be disposed. The lumber support 218 is fixed to the three-dimensional solid knitted fabric supporting member 215 by using a hook and loop fastener or the like. Providing the lumber support 218 in this manner contributes to improvement in stroke feeling in a narrow space.

The above-described biological signal measuring apparatus 200 is arranged inside a skin 1200 covering a seatback frame 1100 of an automobile seat 1000, for example, as shown in FIG. 23. Incidentally, in order to facilitate an arrangement work, it is preferred that the three-dimensional solid knitted fabric 210, the three-dimensional solid knitted fabric supporting member 215, the film 216, the plate-shaped expanded bodies 221, 222, the vibration sensor 230, and the like configuring the biological signal measuring apparatus 200 are unitized in advance.

According to the above-described biological signal measuring apparatus 200, a membrane oscillation (transverse wave) occurs in the plate-shaped expanded bodies 221, 222 and the film 216 having the load-deflection characteristic similar to the load-deflection characteristic of a muscle and a string vibration occurs in the three-dimensional solid knitted fabric 210 having the load-deflection characteristic similar to the load-deflection characteristic of a muscle of a person by a biological signal. Then, the string vibration of the three-dimensional knitted fabric 210 affects the membrane oscillation (transverse wave) of the film 216 and the like again, and these vibration and oscillation serve in an overlapping state. As a result, vibration inputted from a body surface according to occurrence of a biological signal is directly detected by the vibration sensor 230 as a solid vibration amplified due to overlapping thereof with the string vibration and the membrane oscillation (transverse wave) without damping.

In the case of the biological signal measuring apparatus 1 which detects air pressure fluctuation within the air pack 10, shown in FIG. 1 and the like, since a volume and pressure are inversely proportional to each other, it is difficult to detect pressure fluctuation unless the volume of a sealing bag is made small. On the other hand, according to the biological signal measuring apparatus 200 shown in FIG. 21 and FIG. 22, since an amplified solid vibration transmitted via the mechanical amplifying device (the three-dimensional solid knitted fabric 210, the plate-shaped expanded bodies 221, 222, and the film 216 or the film 217) is detected instead of the air pressure fluctuation, the volume (cubic volume) of the apparatus is hardly limited from the viewpoint of a detection sensitivity, so that a vibration with small amplitude as a aortic pulse wave can be detected with a high sensitivity. Therefore, the biological signal measuring apparatus 200 can accommodate persons having various physical bodies. Accordingly, the biological signal measuring apparatus 200 shown in FIG. 21 and FIG. 22 can detect a biological signal with a high sensitivity even under such an environment where the apparatus is utilized by persons having various physical bodies and inputted with various external vibrations like an automobile seat.

Test Example 2

The biological signal measuring device 200 shown in FIG. 22 was mounted to an automobile seat 1000, as shown in FIG. 23, and drink experiments similar to the test example 1 were performed.

Subjects were four healthy Japanese men (G, H, I, J) in their 20s to 40s and they are made to sit on the above-described seat 1000, respectively, so that measurements of their aortic pulse waves were performed. Simultaneously with measurement of the aortic pulse wave, the finger photoplethysmogram was measured by using an optical finger photoplethysmogram sphygmograph (Finger Clip Probe "SR-5C" manufactured by AMCO INC.), and the breath-alcohol concentration was measured by using "ALC-mini" manufactured by TOKAI DENSHI INC.) before and after the measurement of the aortic pulse wave. Ethanol patch tests were preliminarily performed to the subjects on days different from the days on which the alcohol-drinking experiments were conducted on them so that it was confirmed that they were of active type (NN type). Incidentally, regarding the weights and heights of the subjects, the subject G is a subject having a weight of 76 kg and a height of 178 cm, the subject H is a subject having a weight of 64 kg and a height of 167 cm, the subject I is a subject having a weight of 51 kg and a height of 173 cm, and the subject J is a subject having a weight of 61 kg and a height of 174 cm. The other test methods and the like are completely equal to those of the test example 1.

Figure 25:
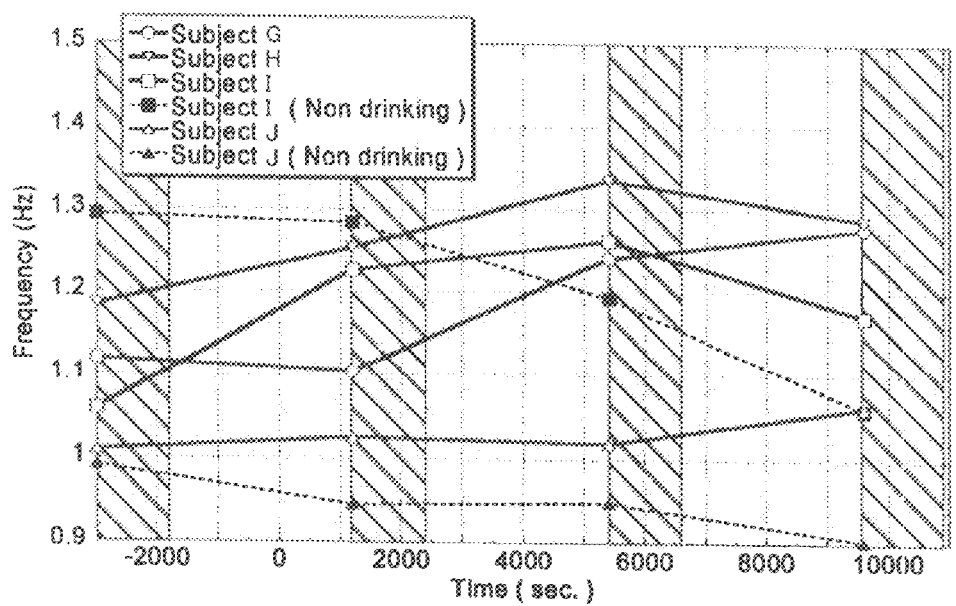
FIGS. 25A to 25F are diagrams showing frequency-analysis results of original waveforms of aortic pulse waves.
Figure 26:
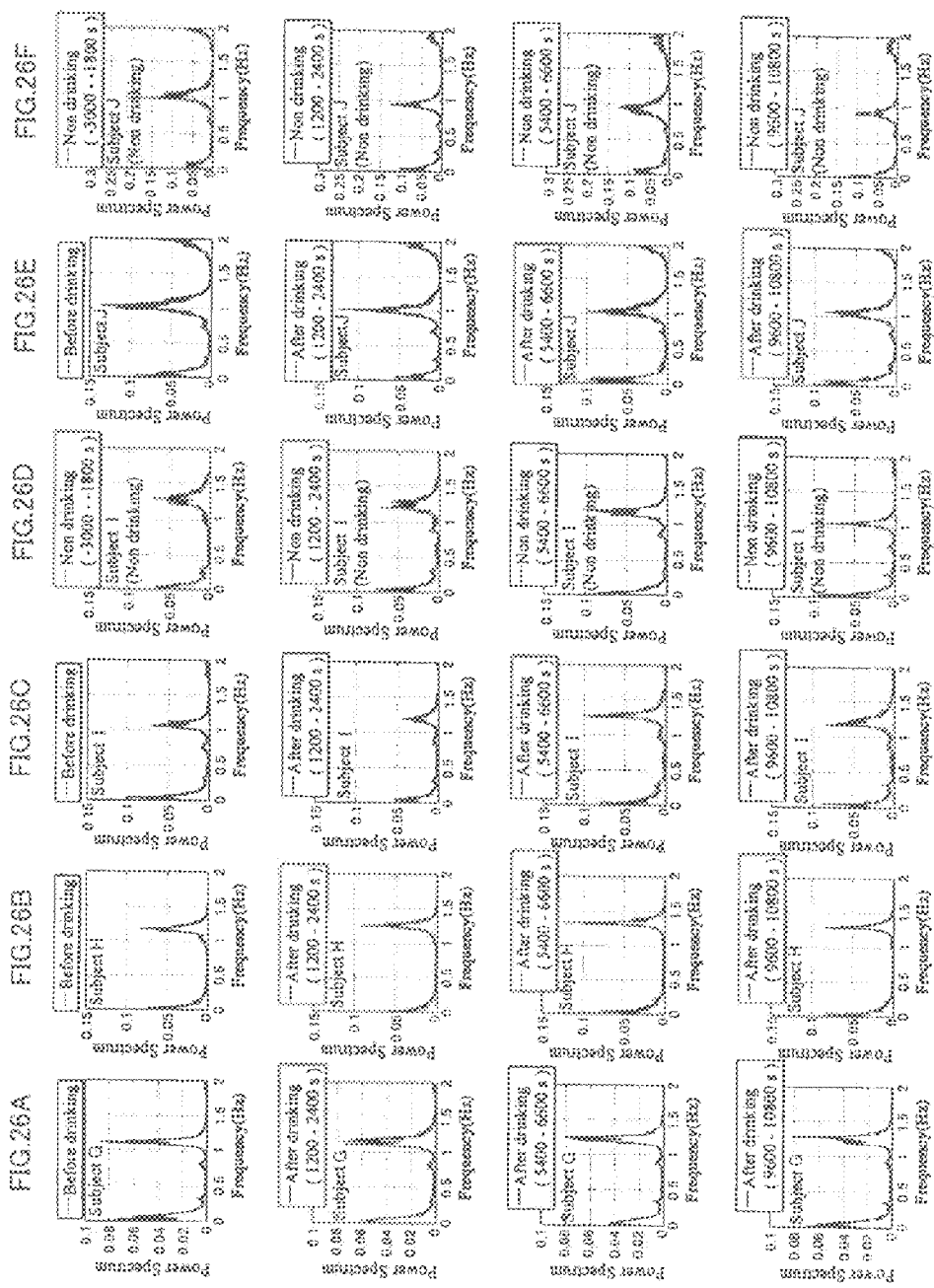
FIG. 26 is a diagram showing time-series changes of the dominant frequencies shown in FIG. 25.
Figure 27:
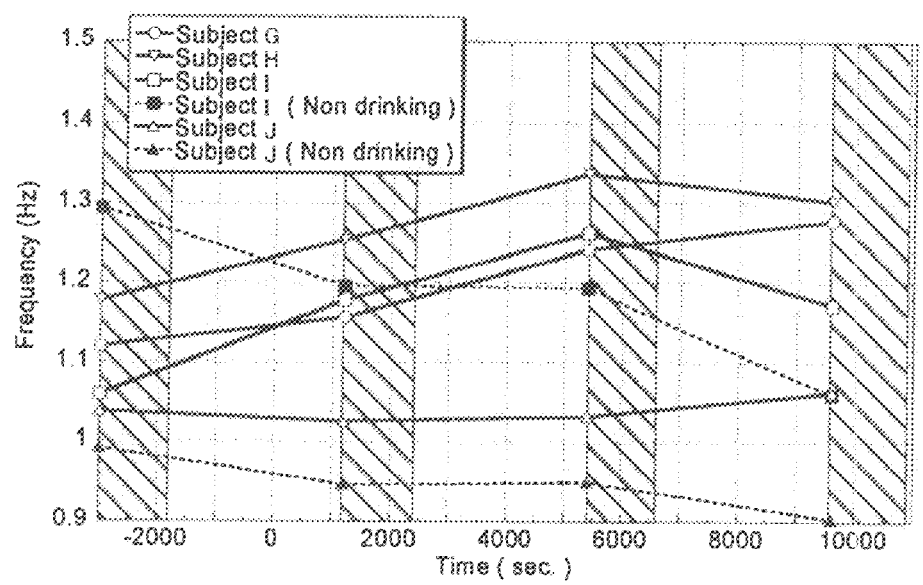
FIGS. 27A to 27F are diagrams showing frequency-analysis results of original waveforms of finger photoplethysmograms shown for verification.
Figure 28:
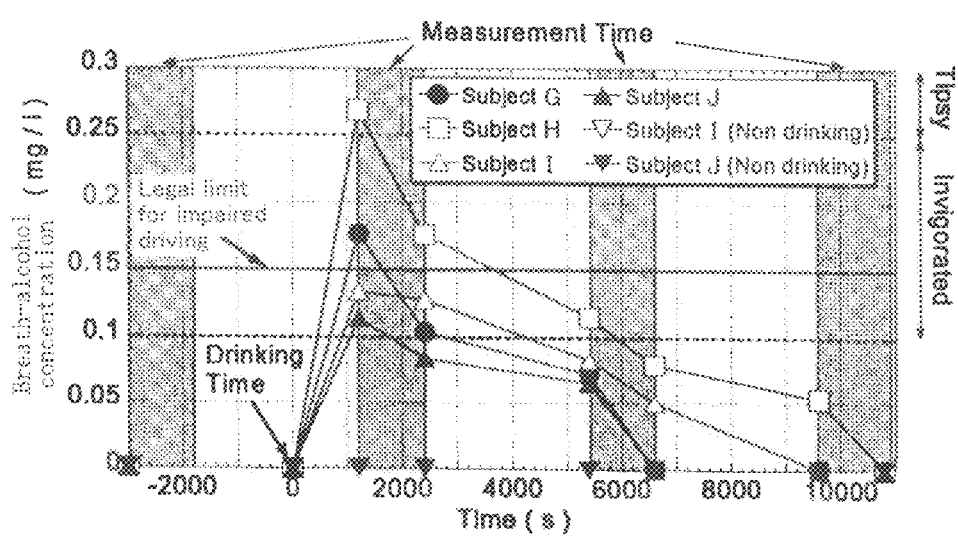
FIG. 28 is a diagram showing time-series changes of the dominant frequencies shown in FIG. 27.

The results are shown in FIG. 24 to FIG. 28. Incidentally, FIG. 24 shows aspects of fluctuations of the breath-alcohol concentrations measured before and after measurements of the aortic pulse waves. Further, regarding the subjects I and J, comparative verification experiments were performed without alcohol drinking according to a test schedule of an approximately the same times as those of the days of the alcohol-drinking experiments on days different from the days on which the alcohol-drinking experiments to them were conducted. FIG. 25 is the frequency analysis result of the original waveforms of the aortic pulse waves, and FIG. 26 shows time-series changes of the dominant frequencies shown in FIG. 25. FIG. 27 shows the frequency analysis result of the original waveforms of the finger photoplethysmograms shown as verification, and FIG. 28 shows time-series changes of the dominant frequencies shown in FIG. 27.

First of all, when the frequency analysis result of the original waveforms of the aortic pulse waves shown in FIG. 25 and the frequency analysis result of the original waveforms of the finger photoplethysmograms shown in FIG. 27 are compared with each other, the aortic pulse waveforms which are biological signals obtained by the biological signal measuring device 200 used in this test example approximately coincide with the finger photoplethysmograms and their peak positions in the respective subjects, from which it is understood that the aortic pulse waves have frequency characteristics approximately equivalent to those of the finger photoplethysmograms.

It is understood from time-series changes of the dominant frequencies shown in FIG. 26 that the dominant frequencies rise due to alcohol drinking regarding the subjects G, H and I. It is thought that this phenomenon is caused by rising of the heart rate due to alcohol drinking. It is understood from comparison with FIG. 24 that the breath-alcohol concentration reaches its peak during the first measurement time after alcohol drinking (in a period from 1200 to 2400 seconds) but the dominant frequency reaches its peak during the second measurement time after alcohol drinking (in a period from 5400 to 6600 seconds) with a slight delay from the former peak.

In the subject J, change of the dominant frequency hardly appears after alcohol drinking. However, the dominant frequency lowers according to time elapsing in a non-drinking state. It is understood from this phenomenon that relative rising of the dominant frequency appears after alcohol drinking even in the case of subject F as compared with a non-drinking case. This point is similar to the case of the subject H. That is, such a phenomenon that the dominant frequency relatively rises according to time elapsing after alcohol drinking as compared with a non-drinking case is captured.

Incidentally, the time-series changes of the dominant frequencies of the aortic pulse waves shown in FIG. 26 show a tendency approximately similar to those of the time-series changes of the dominant frequencies of the finger photoplethysmograms shown in FIG. 28, from which it is understood that it is effective to utilize biological signals obtained from the biological signal measuring device 200 used in this test example.

Figure 29A:
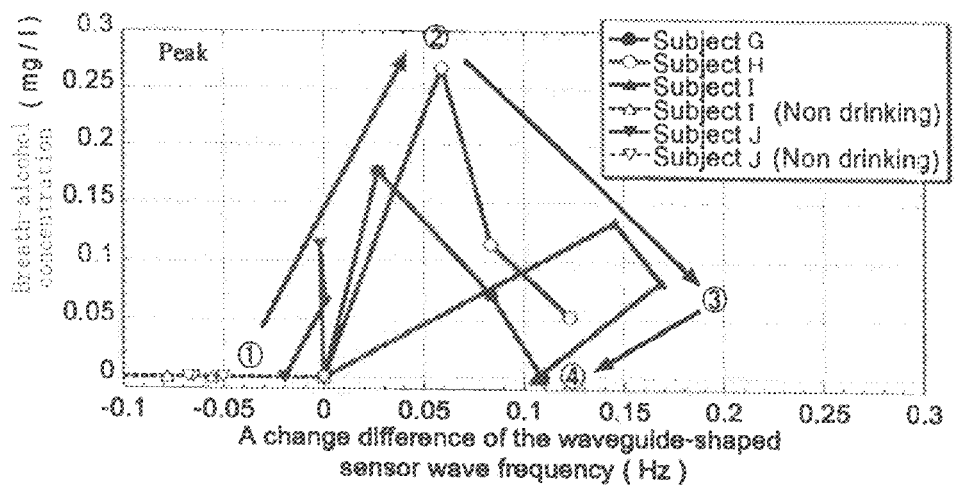
FIGS. 29A and 29B are diagrams capturing correlation between a difference value obtained from a frequency fluctuation time-series waveform and a breath-alcohol concentration, FIG. 29A showing a result of using a frequency fluctuation time-series waveform using a peak detecting method and FIG. 29B showing a result of using a frequency fluctuation time-series waveform using a zero-crossing method.
Figure 29B:
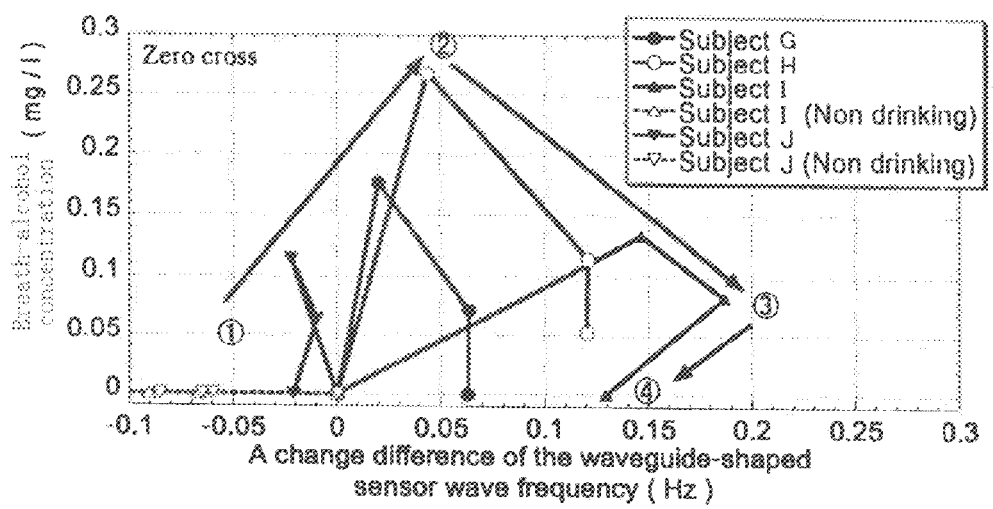

FIGS. 29A and 29B are graphs showing a correlation with the breath-alcohol concentration obtained by processing biological signals (aortic pulse waves) obtained by the biological signal measuring device 200 used in this test example by the frequency fluctuation time-series analyzing and computing means 632 to use the resultant frequency fluctuation time-series waveforms. Specifically, FIGS. 29A and 29B show a correlation of a difference value with the breath-alcohol concentration, the difference value being obtained by obtaining an average value of the frequency fluctuation time-series waveform in a period from 0 to 600 second with reduced influence of sitting fatigue and obtaining a difference value between the average value and an average value before alcohol drinking. Incidentally, FIG. 29A shows the result obtained by using the frequency fluctuation time-series waveform obtained by using a peak detecting method, while FIG. 29B shows the result obtained by using the frequency fluctuation time-series waveform obtained by using a zero-crossing method.

It is understood from FIGS. 29A and 29B that the difference value of the frequency fluctuation increases toward plus according to rising of the breath-alcohol concentration due to alcohol drinking and the frequency fluctuation comes close to the original frequency according to lowering of the breath-alcohol concentration thereafter in both of the peak detecting method and the zero-crossing method. On the other hand, it is understood that the difference value increases toward minus in a non-drinking case. It is understood from this matter that there is a large difference between the non-drinking case and the alcohol-drinking case. Therefore, such a difference value of the frequency fluctuation is obtained so that, when the difference value equal to or more than a predetermined value occurs, the alcohol-drinking state can be estimated. Further, by storing a look-up table between the breath-alcohol concentration and the difference value such as shown in FIGS. 29A and 29B in a computer for each individual, the breath-alcohol concentration can be estimated by calculating the difference value of the frequency fluctuation.

REFERENCE SIGNS LIST

1: biological signal measuring device
10: air pack
11: surface side air pack
111: small airbag
111b: sensor
112: three-dimensional solid knitted fabric
12: back surface side air pack
121: large airbag
122: three-dimensional solid knitted fabric
15: receiving body
100: air-pack unit
20: first elastic member made of expanded resin beads
30: second elastic member made of expanded resin beads
40, 45: three-dimensional solid knitted fabric
500: seat
510: seatback section
511: skin member
512: cushion supporting member
520: seat cushion section
60: alcohol-drinking detecting system
600: alcohol-drinking analyzing and estimating section
610: frequency dynamic information processing means
621: dominant frequency time-series waveform computing means
622: dominant frequency fluctuation time-series analyzing and computing means
623: dominant frequency slope time-series analyzing and computing means
631: frequency computing means
632: frequency fluctuation time-series analyzing means
633: frequency slope time-series analyzing means
650: alcohol-drinking determining means

The invention claimed is:

1. An alcohol-drinking detecting system to analyze a biological signal obtained from an upper body of a person by a biological signal measuring device to estimate presence/absence of alcohol in the body, the alcohol-drinking detecting system comprising:
circuitry configured to:
obtain, from a time-series waveform of the biological signal, a time-series fluctuation regarding a frequency of the time series-waveform; and
determine an alcohol-drinking state when a tendency of the time-series fluctuation regarding the frequency obtained from the circuitry is separated from a tendency of a time-series fluctuation regarding the frequency at a non-drinking time,
obtain a time-series waveform of a frequency in the time-series waveform of the biological signal;
perform moving calculation for obtaining, in the time-series waveform of the frequency of the biological signal obtained by the circuitry, a slope of the frequency for each of predetermined time windows set in a predetermined overlapping time to output a time-series change of the slope of the frequency obtained for each time window as a frequency slope time-series waveform;
determine the alcohol-drinking state according to whether or not, regarding a difference of an integral value of a positive slope and a difference of an integral value of a negative slope obtained by dividing the frequency slope time-series waveform into the positive slope and the negative slope to integrate the respective positive and negative slopes and comparing integral values of the positive slope and the negative slope with those in a normal state before alcohol drinking, the difference of the integral value of the positive slope decreases to a predetermined difference or more and the difference of the integral value of the negative slope increases to a predetermined difference or more; and output the alcohol-drinking state as determined by the circuitry.

2. An alcohol-drinking detecting system to analyze a biological signal obtained from an upper body of a person by a biological signal measuring device to estimate presence/absence of alcohol in the body, the alcohol-drinking detecting system comprising:
circuitry configured to:
obtain, from a time-series waveform of the biological signal, a time-series fluctuation regarding a frequency of the time series-waveform; and
determine an alcohol-drinking state when a tendency of the time-series fluctuation regarding the frequency obtained from the circuitry is separated from a tendency of a time-series fluctuation regarding the frequency at a non-drinking time,
obtain a time-series waveform of a frequency in the time-series waveform of the biological signal;
perform moving calculation for obtaining, in the time-series waveform of the frequency of the biological signal obtained by the circuitry, an average value of the frequency for each of predetermined time windows set in a predetermined overlapping time to output a time-series change of the average value of the frequency obtained for each time window as a frequency fluctuation time-series waveform;
perform moving calculation for obtaining, in the time-series waveform of the frequency of the biological signal obtained by the circuitry, a slope of the frequency for each of predetermined time windows set in a predetermined overlapping time to output a time-series change of a slope of the frequency obtained for each time window as a frequency slope time-series waveform;
determine the alcohol-drinking state according to whether or not a base line position of the frequency fluctuation time-series waveform is higher than that at a non-drinking state and whether or not, regarding a difference of an integral value of a positive slope and a difference of an integral value of a negative slope obtained by dividing the frequency slope time-series waveform into the positive slope and the negative slope to integrate the respective positive and negative slopes and comparing the integral values of the positive slope and the negative slope with those in a normal state before alcohol drinking, the difference of the integral value of the positive slope decreases to a predetermined difference or more and the difference of the integral value of the negative slope increases to a predetermined difference or more; and
output the alcohol-drinking state as determined by the circuitry.

3. A non-transitory computer readable medium including executable instructions, which when executed by circuitry cause the circuitry to execute an alcohol-drinking analyzing and estimating process to analyze a biological signal obtained from an upper body of a person by a biological signal measuring device to estimate presence/absence of alcohol in the body, the alcohol-drinking analyzing and estimating process comprising:
obtaining, from a time-series waveform of the biological signal, a time-series fluctuation regarding a frequency of the time series-waveform;
determining an alcohol-drinking state when a tendency of the time-series fluctuation regarding the frequency obtained by the obtaining is separated from a tendency of a time-series fluctuation regarding the frequency at a non-drinking time;
obtaining a time-series waveform of a frequency in the time-series waveform of the biological signal;
performing moving calculation for obtaining, in the time-series waveform of a frequency of the biological signal, a slope of the frequency for each of predetermined time windows set in a predetermined overlapping time to output a time-series change of the slope of the frequency obtained for each time window as a frequency slope time-series waveform;
determining the alcohol-drinking state according to whether or not, regarding a difference of an integral value of a positive slope and a difference of an integral value of a negative slope obtained by dividing the frequency slope time-series waveform into the positive slope and the negative slope to integrate the respective positive and negative slopes and comparing integral values of the positive slope and the negative slope with those in a normal state before alcohol drinking, the difference of the integral value of the positive slope decreases to a predetermined difference or more and the difference of the integral value of the negative slope increases to a predetermined difference or more; and
outputting the alcohol-drinking state as determined by the circuitry.

4. A non-transitory computer readable medium including executable instructions, which when executed by circuitry cause the circuitry to execute an alcohol-drinking analyzing and estimating process to analyze a biological signal obtained from an upper body of a person by a biological signal measuring device to estimate presence/absence of alcohol in the body, the alcohol-drinking analyzing and estimating process comprising:
obtaining, from a time-series waveform of the biological signal, a time-series fluctuation regarding a frequency of the time series-waveform;
determining an alcohol-drinking state when a tendency of the time-series fluctuation regarding the frequency obtained by the obtaining is separated from a tendency of a time-series fluctuation regarding the frequency at a non-drinking time;
obtaining a time-series waveform of a frequency in the time-series waveform of the biological signal;
performing moving calculation for obtaining, in the time-series waveform of a frequency of the biological signal, an average value of the frequency for each of predetermined time windows set in a predetermined overlapping time to output a time-series change of the average value of the frequency obtained for each time window as a frequency fluctuation time-series waveform;
performing moving calculation for obtaining, in the time-series waveform of the frequency of the biological signal, a slope of the frequency for each of predetermined time windows set in a predetermined overlapping time to output a time-series change of a slope of the frequency obtained for each time window as a frequency slope time-series waveform;
determining the alcohol-drinking state according to whether or not a base line position of the frequency fluctuation time-series waveform is higher than that at a non-drinking state and whether or not, regarding a difference of an integral value of a positive slope and a difference of an integral value of a negative slope obtained by dividing the frequency slope time-series waveform into the positive slope and the negative slope to integrate the respective positive and negative slopes and comparing the integral values of the positive slope and the negative slope with those in a normal state before alcohol drinking, the difference of the integral value of the positive slope decreases to a predetermined difference or more and the difference of the integral value of the negative slope increases to a predetermined difference or more; and
outputting the alcohol-drinking state as determined by the circuitry.

* * * * *